US009205006B2

(12) United States Patent
Cheng et al.

(10) Patent No.: US 9,205,006 B2
(45) Date of Patent: Dec. 8, 2015

(54) ABSORBENT ARTICLES WITH NONWOVEN SUBSTRATES HAVING FIBRILS

(71) Applicant: The Procter & Gamble Company, Cincinnati, OH (US)

(72) Inventors: Calvin Hoi Wung Cheng, Cincinnati, OH (US); Olaf Erik Alexander Isele, West Chester, OH (US); Brian Udengaard, Lystrup (DK)

(73) Assignee: The Procter & Gamble Company, Cincinnati, OH (US)

( * ) Notice: Subject to any disclaimer, the term of this patent is extended or adjusted under 35 U.S.C. 154(b) by 216 days.

(21) Appl. No.: 13/833,311

(22) Filed: Mar. 15, 2013

(65) Prior Publication Data

US 2014/0276512 A1 Sep. 18, 2014

(51) Int. Cl.
| | |
|---|---|
| *A61F 13/15* | (2006.01) |
| *A61F 13/53* | (2006.01) |
| *A61L 15/34* | (2006.01) |
| *A61F 13/511* | (2006.01) |
| *A61F 13/514* | (2006.01) |
| *A61F 13/51* | (2006.01) |

(52) U.S. Cl.
CPC ........... *A61F 13/53* (2013.01); *A61F 13/51113* (2013.01); *A61F 13/51405* (2013.01); *A61L 15/34* (2013.01); *A61F 2013/51002* (2013.01); *A61F 2013/51004* (2013.01); *A61F 2013/51007* (2013.01); *A61F 2013/51009* (2013.01); *A61F 2013/51059* (2013.01)

(58) Field of Classification Search
CPC ........................ A61F 13/530868; A61F 13/51
USPC ........... 604/367, 385.101, 381, 382, 359, 360
See application file for complete search history.

(56) References Cited

U.S. PATENT DOCUMENTS

| | | | |
|---|---|---|---|
| 3,785,918 | A | 1/1974 | Kawai et al. |
| 3,870,567 | A | 3/1975 | Palmer |
| 4,304,234 | A | 12/1981 | Hartmann |
| 4,578,414 | A | 3/1986 | Sawyer |
| 4,818,594 | A | 4/1989 | Albien et al. |
| 5,045,387 | A | 9/1991 | Schmalz |
| 5,198,292 | A | 3/1993 | Lerner et al. |
| 5,283,023 | A | 2/1994 | Nohr |

(Continued)

FOREIGN PATENT DOCUMENTS

| | | |
|---|---|---|
| EP | 862402 | 9/1998 |
| EP | 2 266 514 | 12/2010 |

(Continued)

OTHER PUBLICATIONS

International Search Report and Written Opinion, PCT/US2014/022905 date of mailing May 23, 2014.

(Continued)

*Primary Examiner* — Jacqueline Stephens
(74) *Attorney, Agent, or Firm* — Christian M. Best

(57) ABSTRACT

The present disclosure is directed, in part, to an absorbent article comprising a liquid pervious material, a liquid impervious material, and an absorbent core disposed at least partially intermediate the liquid pervious material and the liquid impervious material. The absorbent article comprises one or more nonwoven substrates each comprising one or more layers of fibers. A plurality of the fibers each comprise a plurality of fibrils extending outwardly from a surface of the fibers. The plurality of fibrils comprise a lipid ester.

39 Claims, 24 Drawing Sheets

(56) References Cited

U.S. PATENT DOCUMENTS

| | | |
|---|---|---|
| 5,300,167 A | 4/1994 | Nohr |
| 5,593,768 A | 1/1997 | Gessner |
| 5,653,930 A | 8/1997 | Noda et al. |
| 5,780,368 A | 7/1998 | Noda et al. |
| 6,117,801 A | 9/2000 | McGinty et al. |
| 6,203,889 B1 | 3/2001 | Quincy |
| 6,300,258 B1 | 10/2001 | Stano |
| 6,353,149 B1 | 3/2002 | Stone |
| 6,602,386 B1 | 8/2003 | Shimizu et al. |
| 6,686,303 B1 | 2/2004 | Haynes et al. |
| 6,699,806 B1 | 3/2004 | Shimizu et al. |
| 6,713,011 B2 * | 3/2004 | Chu et al. ............... 264/465 |
| 6,767,498 B1 | 7/2004 | Yu et al. |
| 6,818,295 B2 | 11/2004 | Bond et al. |
| 6,855,422 B2 | 2/2005 | Magill et al. |
| 6,890,649 B2 | 5/2005 | Hobbs et al. |
| 6,946,506 B2 | 9/2005 | Bond et al. |
| 7,150,912 B2 | 12/2006 | Mizutani et al. |
| 7,241,497 B2 | 7/2007 | Magill et al. |
| 7,267,789 B2 | 9/2007 | Chhabra et al. |
| 7,291,300 B2 | 11/2007 | Chhabra et al. |
| 7,781,353 B2 | 8/2010 | Snowden |
| 7,981,226 B2 | 7/2011 | Pourdeyhimi et al. |
| 8,026,188 B2 | 9/2011 | Mor |
| 8,168,550 B2 | 5/2012 | Collias et al. |
| 8,173,559 B2 | 5/2012 | Collias et al. |
| 2002/0169429 A1 | 11/2002 | Li |
| 2003/0091803 A1 | 5/2003 | Bond et al. |
| 2003/0178166 A1 | 9/2003 | Takeuchi et al. |
| 2003/0203695 A1 | 10/2003 | Polanco et al. |
| 2004/0005457 A1 | 1/2004 | DeLucia et al. |
| 2004/0119207 A1 | 6/2004 | Stone |
| 2004/0127128 A1 | 7/2004 | Thomas |
| 2004/0161994 A1 | 8/2004 | Arora et al. |
| 2005/0095695 A1 | 5/2005 | Shindler et al. |
| 2005/0130539 A1 | 6/2005 | Allen |
| 2006/0147804 A1 | 7/2006 | Yamamoto et al. |
| 2006/0154548 A1 | 7/2006 | Sheehan et al. |
| 2006/0172641 A1 | 8/2006 | Hennige et al. |
| 2007/0077427 A1 | 4/2007 | Dugan |
| 2007/0082573 A1 | 4/2007 | Noda et al. |
| 2007/0232179 A1 | 10/2007 | Polat et al. |
| 2008/0179777 A1 | 7/2008 | Wild |
| 2010/0024281 A1 | 2/2010 | Lemke |
| 2010/0028638 A1 | 2/2010 | Reichardt et al. |
| 2010/0041292 A1 | 2/2010 | Kim et al. |
| 2010/0272938 A1 | 10/2010 | Mitchell et al. |
| 2010/0322989 A1 | 12/2010 | Martin |
| 2010/0330861 A1 | 12/2010 | Mor |
| 2011/0117176 A1 | 5/2011 | Klun et al. |
| 2011/0196332 A1 | 8/2011 | Cheng |
| 2012/0100772 A1 | 4/2012 | Hummelgaard |
| 2012/0109090 A1 | 5/2012 | Reichardt |
| 2012/0122363 A1 | 5/2012 | Owens |
| 2012/0296036 A1 | 11/2012 | Allen et al. |
| 2012/0321869 A1 | 12/2012 | Allen et al. |
| 2012/0321870 A1 | 12/2012 | Allen et al. |
| 2012/0321871 A1 | 12/2012 | Bond et al. |
| 2013/0012093 A1 | 1/2013 | Bond |
| 2014/0259483 A1 | 9/2014 | Cheng et al. |
| 2014/0259579 A1 | 9/2014 | Cheng et al. |
| 2014/0272223 A1 | 9/2014 | Cheng et al. |
| 2014/0272359 A1 | 9/2014 | Cheng et al. |

FOREIGN PATENT DOCUMENTS

| | | | |
|---|---|---|---|
| GB | 1225824 | * 3/1968 | ............... D01D 5/00 |
| GB | 200205029 | 4/2002 | |
| JP | 62129054 | 6/1987 | |
| JP | 62133164 | 6/1987 | |
| JP | 62268861 | 11/1987 | |
| JP | 1272861 | 10/1989 | |
| JP | 2191759 | 7/1990 | |
| JP | 3279452 | 12/1991 | |
| JP | 4091224 | 3/1992 | |
| JP | 4136251 | 5/1992 | |
| JP | 5051818 | 3/1993 | |
| JP | 6070954 | 3/1994 | |
| JP | 6245952 | 9/1994 | |
| JP | 7258964 | 10/1995 | |
| JP | 8158229 | 6/1996 | |
| JP | 9049160 | 2/1997 | |
| JP | 9111630 | 4/1997 | |
| JP | 9273061 | 10/1997 | |
| JP | 2000178865 | 6/2000 | |
| JP | 2002061060 | 2/2002 | |
| JP | 2002263137 | 9/2002 | |
| JP | 2003138428 | 5/2003 | |
| JP | 2003301358 | 10/2003 | |
| JP | 2004169261 | 6/2004 | |
| JP | 2004285538 | 10/2004 | |
| JP | 2005330637 | 12/2005 | |
| JP | 2007113145 | 5/2007 | |
| JP | 2007154380 | 6/2007 | |
| JP | 2008002037 | 1/2008 | |
| JP | 2008095254 | 4/2008 | |
| JP | 2008161584 | 7/2008 | |
| JP | 2009150005 | 7/2009 | |
| JP | 2009228157 | 10/2009 | |
| WO | WO 95/23249 | 8/1995 | |
| WO | WO 95/23250 | 8/1995 | |
| WO | WO 98/08475 | 3/1998 | |
| WO | WO9906207 | 2/1999 | |
| WO | WO 98/31735 | 10/1999 | |
| WO | WO0190230 | 11/2001 | |
| WO | WO 2005/042824 | 5/2005 | |
| WO | WO 2010/149239 | 12/2010 | |
| WO | WO 2011/090425 | 7/2011 | |
| WO | WO 2012/162083 | 11/2012 | |
| WO | WO 2012/162084 | 11/2012 | |
| WO | WO 2012/162085 | 11/2012 | |
| WO | WO 2012/162092 | 11/2012 | |
| WO | WO 2012/162135 | 11/2012 | |
| WO | WO 2012/162146 | 11/2012 | |
| WO | WO 2012/162149 | 11/2012 | |

OTHER PUBLICATIONS

All Office Actions, U.S. Appl. No. 13/833,390.
All Office Actions, U.S. Appl. No. 13/833,456.
All Office Actions, U.S. Appl. No. 13/833,503.
All Office Actions, U.S. Appl. No. 14/247,588.
All Office Actions, Responses and Claims for U.S. Appl. No. 13/833,390.
Stearin, Wikipedia. http:/en.wikipedia.org/wiki/Stearin. Retrieved Jan. 26, 2012.
Glyceryl Monostearate Materail Safety Data Sheet. Spectrum. Printed Sep. 27, 2007.
All Office Actions, Responses and Claims, U.S. Appl. No. 13/833,390.
All Office Actions, Responses and Claims, U.S. Appl. No. 13/833,456.
All Office Actions, Responses and Claims, U.S. Appl. No. 13/833,503.
All Office Actions, Responses and Claims, U.S. Appl. No. 14/247,588.
All Office Actions, Responses and Claims, U.S. Appl. No. 14/861,004.
All Office Actions, Responses, and Claims, U.S. Appl. No. 13/833,390.
All Office Actions, Responses, and Claims, U.S. Appl. No. 13/833,456.
All Office Actions, Responses, and Claims, U.S. Appl. No. 13/833,503.
All Office Actions, Response,s and Claims, U.S. Appl. No. 14/247,588.

* cited by examiner

ABSORBENT ARTICLES WITH NONWOVEN SUBSTRATES HAVING FIBRILS

FIELD

The present disclosure generally relates to absorbent articles with nonwoven substrates having fibrils and methods for forming the same.

BACKGROUND

Nonwoven substrates may be useful in a wide variety of applications. Various nonwoven substrates may comprise spunbond-meltblown-spunbond ("SMS") substrates comprising outer layers of spunbond thermoplastics (e.g., polyolefins) and interior layers of meltblown thermoplastics. Some nonwoven substrates, either in addition to or in place of the meltblown thermoplastics, may comprise fine fibers (i.e., fibers having a diameter of less than one micrometer ("N-fibers") to create "SMNS" substrates or "SNS" substrates, for example. Such nonwoven substrates may comprise spunbond layers which are durable and internal meltblown layers and/or fine fiber layers which are porous but which may inhibit fast strikethrough of fluids, such as bodily fluids, for example, or the penetration of bacteria through the nonwoven substrates.

Absorbent articles such as diapers, training pants, adult incontinence products, and feminine hygiene products utilize nonwoven substrates for many purposes. For many applications, the barrier properties of the nonwoven substrates play an important role in the performance of the nonwoven substrates, such as the performance as a barrier to fluid penetration, for example. Absorbent articles may comprise multiple elements, such as a liquid pervious material or topsheet intended to be placed next to the wearer's skin, a liquid impervious material or backsheet intended to be placed proximate to or on the outer surface of the absorbent article, various barrier layers or cuffs, and an absorbent core disposed at least partially intermediate the liquid pervious material and the liquid impervious material.

Frequently, films, such as elastomeric films, are used in the manufacturing of various components of absorbent articles and other articles of commerce. For example, films may be used in liquid pervious layers, liquid impervious layers, barrier cuffs, barrier layers, side panels, or in other components of absorbent articles or other articles of commerce. Films provide a high resistance to fluid flow and thus offer ideal barrier performance. This applies even to formed, apertured films where the film area around the apertures provides excellent protection against fluid flow and rewet. Films, however, are quite expensive and less comfortable to a wearer compared to nonwoven substrates. As such, manufacturers of articles of commerce, such as absorbent articles, that incorporate films are usually trying to reduce the amount of the films in their products. What is needed are nonwoven substrates that can match, or come close to matching, the specific advantageous properties of the films, such as low surface tension fluid strikethrough times, while providing comfort to the users and cost advantages to manufacturers. Also, what is needed are nonwoven substrates that have lower basis weights compared to conventional nonwoven substrates, but that have the same fluid strikethrough times as the conventional nonwoven substrates to again save material costs for manufacturers.

SUMMARY

In one form, the present disclosure is directed, in part, to an absorbent article comprising a liquid pervious material, a liquid impervious material, and an absorbent core disposed at least partially intermediate the liquid pervious material and the liquid impervious material. The absorbent article comprises a nonwoven substrate comprising one or more layers of fibers. A plurality of the fibers each comprise a plurality of fibrils extending outwardly from a surface of the fibers. The plurality of fibrils comprise a lipid ester.

In another form, the present disclosure is directed, in part, to an absorbent article comprising a liquid pervious material, a liquid impervious material, and an absorbent material positioned at least partially intermediate the liquid pervious material and the liquid impervious material. The absorbent article comprises a nonwoven substrate comprising one or more layers of fibers. The layer of fibers comprises a plurality of bonds with each bond comprising a bond area. A plurality of fibrils extend outwardly from a surface of at least one of the bond areas.

In another form, the present disclosure is directed, in part, to absorbent article comprising a nonwoven substrate comprising one or more layers of fibers. A plurality of the fibers comprise fibrils extending outwardly therefrom only after a time period. The time period is greater than about 24 hours post-nonwoven substrate formation under ambient conditions.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION

Figure 1:
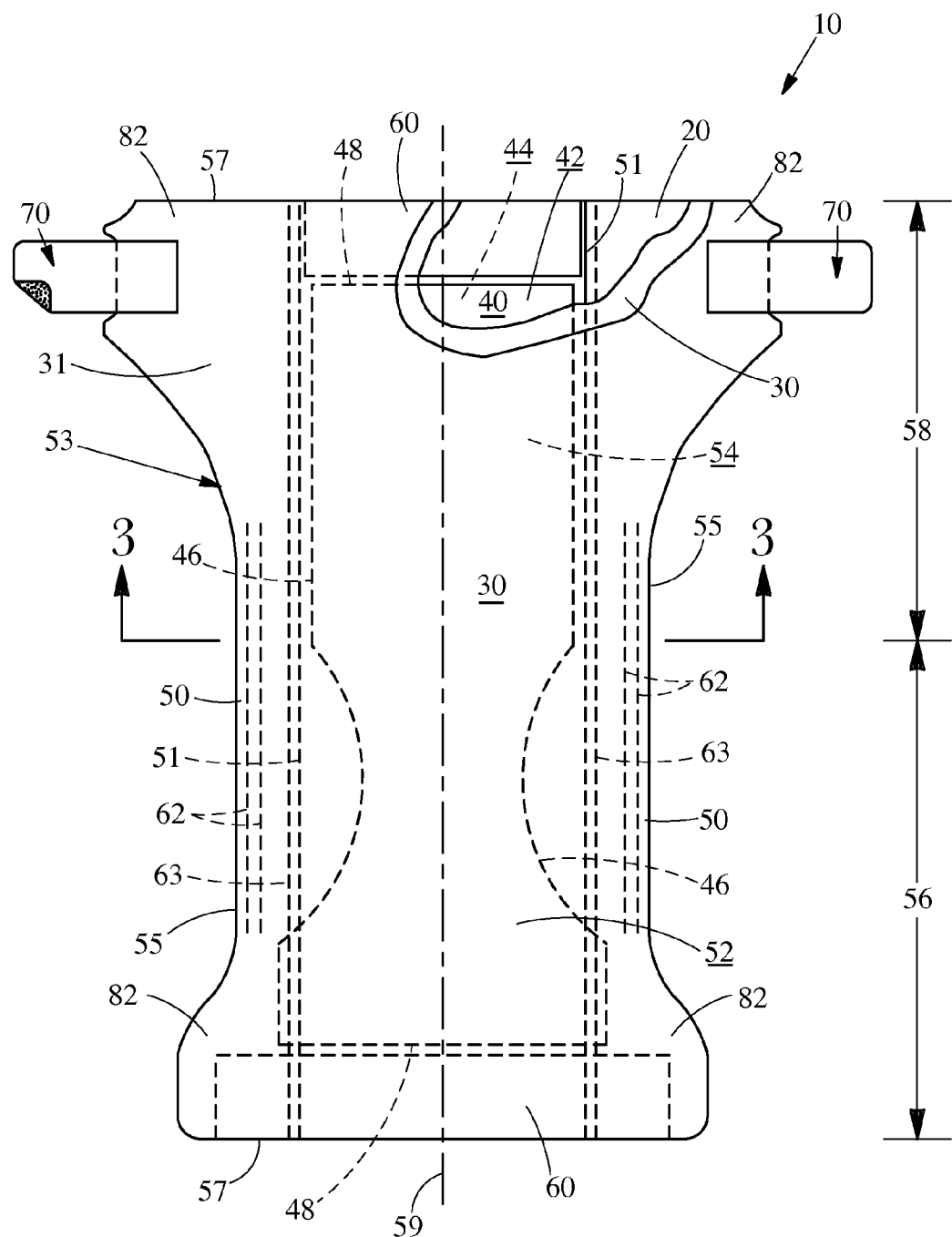
FIG. 1 is a plan view of an absorbent article (laid flat without elastic contraction) with the garment-facing surface toward the viewer in accordance with a non-limiting embodiment.

Various non-limiting embodiments of the present disclosure will now be described to provide an overall understanding of the principles of the structure, function, manufacture, and use of the absorbent articles having nonwoven substrates with fibrils and methods for forming the same disclosed herein. One or more examples of these non-limiting embodiments are illustrated in the accompanying drawings. Those of ordinary skill in the art will understand that the absorbent articles having nonwoven substrates with fibrils and methods for forming the same specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Definitions:

In this description, the following terms have the following meanings:

The term "absorbent article" refers to disposable devices such as infant, child, or adult diapers or incontinence products, training pants, sanitary napkins, tampons, and the like which are placed against or in proximity to the body or a natural orifice of the body of the wearer to absorb and contain the various exudates (e.g., urine, BM, menses) discharged from the body. Certain absorbent articles may comprise a topsheet or liquid pervious layer, a backsheet or liquid impervious layer, and an absorbent core positioned at least partially intermediate the topsheet and the backsheet. The articles may also comprise an acquisition system (which may be comprised of one or several layers), and typically other components. Example absorbent articles of the present disclosure will be further illustrated in the below description and in the figures in the form of a taped diaper and a sanitary napkin. Nothing in this description should be considered limiting the scope of the claims based on the example absorbent articles illustrated and described. As such, the present disclosure applies to any suitable form of absorbent articles (e.g., training pants, adult incontinence products, sanitary napkins). For the avoidance of doubt, absorbent articles do not include wipes. Wipes are defined hereinafter and are also within the scope of present disclosure.

The term "ambient conditions" is defined as typical post-nonwoven substrate and/or absorbent article manufacturing conditions, nonwoven substrate and/or absorbent article storage conditions, and more specifically 20 degrees C.+/−7 degrees C. at a relative humidity of 50%+/−30%.

The term "article of commerce" includes any products, such as absorbent articles, wipes (wet or dry), cleaning or dusting substrates, filters, filter media, toothbrushes, or batteries, for example.

The term "basis weight" is defined by the Basis Weight Test set forth below. Basis weight is set forth in grams/m² (gsm).

The term "bond area" refers to the area of an individual bond site.

The term "cross direction" refers to a direction that is generally perpendicular to the machine direction.

The term "diameter" when referring to fibers is defined by the Fiber Diameter and Denier Test set forth below. Diameter of fibers is set forth in microns.

The term "elastic strand" or "elastic member" refers to a ribbon or strand (i.e., great length compared to either width and height or diameter of its cross-section) as may be part of the inner or outer cuff gathering component of an article.

The term "fiber" refers to any type of artificial fiber, filament, or fibril, whether continuous or discontinuous, produced through a spinning process, a meltblowing process, a melt fibrillation or film fibrillation process, or an electrospinning production process, or any other suitable process.

The term "film" refers to a polymeric material, having a skin-like structure, and it does not comprise individually distinguishable fibers. Thus, "film" does not include a nonwoven material. For purposes herein, a skin-like material may be perforated, apertured, or micro-porous and still be deemed a "film."

The term "fibrils" refers to projections, elongate projections, or bumps that extend outwardly from a surface or generally radially outwardly from an outer surface of a fiber. In some instances, the projections, elongate projections, or bumps may extend radially outwardly relative to a longitudinal axis of the fiber. Radially outwardly means in the range of 1 to 89 degrees relative to the longitudinal axis. In still other instances, the projections, elongate projections, or bumps may extend radially outwardly from a surface of a fiber at least in a longitudinal central third of the fiber. The projections, elongate projections, or bumps comprise, consist of, or consist essentially of (e.g., 51% to 100% or 51% to 99%), melt additives, such as lipid esters. The projections, elongate projections, or bumps grow from the fibers post-nonwoven substrate formation only after a time period (e.g., 6-100 hours) under ambient conditions. Fibrils can be viewed using an SEM at, at least 1,000 times magnification.

The term "hydrophobic" refers to a material or composition having a contact angle greater than or equal to 90° according to The American Chemical Society Publication "Contact Angle, Wettability, and Adhesion," edited by Robert F. Gould and copyrighted in 1964. In certain embodiments, hydrophobic surfaces may exhibit contact angles greater than 120°, greater than 140°, or even greater than 150°. Hydrophobic liquid compositions are generally immiscible with water. The term "hydrophobic melt additive" refers to a hydrophobic composition that has been included as an additive to a hot melt composition (i.e., blended into a thermoplastic melt), which is then formed into fibers and/or a substrate (e.g., by spunbonding, meltblowing, melt fibrillation, or extruding).

The term "hydrophobic surface coating" refers to a composition that has been applied to a surface in order to render the surface hydrophobic or more hydrophobic. "Hydrophobic surface coating composition" means a composition that is to be applied to a surface of a substrate, such as a nonwoven substrate, in order to provide a hydrophobic surface coating.

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

The term "low surface tension fluid" refers to a fluid having a surface tension of 32 mN/m+/−1.0 mN/m.

The term "low surface tension fluid strikethrough time" is defined by the Low Surface Tension Fluid Strikethrough Time Test set forth below. Low Surface Tension Fluid Strikethrough Time is set forth in seconds.

The term "machine direction" (MD) refers to the direction of material flow through a process.

The term "calender bond" or "thermal bond" refers to a bond formed between fibers of a nonwoven by pressure and temperature such that the polymeric fibers within the bond melt or fuse together to form a compressed, flat area which may be a continuous film-like material. The term "calender bond" does not comprise a bond formed using an adhesive nor through the use of pressure only as defined by mechanical bond below. The term "thermal bonding" or "calender bonding" refers to the process used to create the thermal bond.

The term "mechanical bond" refers to a bond formed between two materials by pressure, ultrasonic attachment, and/or other mechanical bonding process without the intentional application of heat. The term mechanical bond does not comprise a bond formed using an adhesive.

The term "layer" refers to one sheet or ply of a nonwoven or other material.

The term "substrate" refers to a sheet-like structure of one or more layers such as a nonwoven substrate.

The term "titer" refers to the longitudinal density as measured in terms of mass per unit length of a fiber.

The term "denier" refers to a unit of fineness of a fiber that is equal to the weight (in grams) per 9000 m of fiber.

The term "mass-average diameter" refers to a mass-weighted arithmetic mean diameter of fibers calculated from the fiber diameter, which is measured by the Fiber Diameter and Denier Test set forth below. Mass-average diameter of fibers is calculated by the Fiber Diameter Calculations set forth below. The mass-average diameter of fibers is set forth in microns.

The term "number-average diameter," alternatively "average diameter", refers to an arithmetic mean diameter of fibers calculated from the fiber diameter, which is measured by the Fiber Diameter and Denier Test set forth below. Number-average diameter of fibers is calculated by the Fiber Diameter Calculations set forth below. The number-average diameter of fibers is set forth in microns.

Nonwoven substrates that have properties that are the same as or come close to matching some film properties are desired. One film property that would be advantageous in a nonwoven material is the film's ability to be fluid impervious or substantially fluid impervious. Films are typically less breathable, less comfortable, and generally noisier under movement than nonwoven materials, unless rendered more nonwoven-like with expensive manufacturing methods. As such, nonwoven materials that have film-like, or close to film-like, fluid permeability properties are desired because of the huge cost savings and greater comfort to the user associated with the same. In an embodiment, the present disclosure provides nonwoven substrates having increased fluid barrier properties. In another embodiment, the present disclosure provides nonwoven substrates having one or more layers of fibers, wherein the nonwoven substrates have certain specific surface areas that are higher than specific surface areas of conventional nonwoven substrates. In an embodiment, a nonwoven substrate of the present disclosure may comprise one or more layers of fibers, wherein a plurality of fibrils may extend outwardly, or radially outwardly, from a surface of at least some of the fibers in the one or more layers of fibers. The fibrils can lead to decreased fluid (i.e., liquid or gas) permeability, especially liquid, in the layer of fibers and the nonwoven substrate as a whole. A nonwoven substrate may have all layers having fibers comprising fibrils or less than all layers having fibers with fibrils. Stated another way, some layers may have fibers that are free of fibrils while other layers may have fibers with fibrils. Some layers may have fibers with fibrils and fibers without fibrils. The specific surface areas of the nonwoven substrates and the fibers with fibrils will be discussed in further detail below after a more general description of an example absorbent article for use with the nonwoven substrates of the present disclosure. Wipes, packages, and packaging materials that use the nonwoven substrates discussed herein are also within the scope of the present disclosure. These will also be discussed in further detail below.

Nonwoven substrates may comprise sheets of individual nonwoven layers of fibers, filaments, or a combination of fibers and filaments, bonded together using mechanical, thermal, or chemical bonding processes. Nonwoven substrates may be formed as relatively flat, porous sheets made directly from individual fibers, including staple fibers, directly from molten plastic, from plastic films, and/or some combination of the aforementioned. Some nonwoven substrates may be strengthened or reinforced by a backing sheet, for example. Nonwoven substrates may be engineered fabrics that may be a limited life, single-use fabrics, or a very durable, reusable fabrics. In various embodiments, nonwoven substrates provide specific functions, such as absorbency, liquid repellency, resilience, stretch, opacity softness, and/or strength. These properties are often combined to create nonwoven substrates suited for specific applications, while achieving a good balance between product useful life and cost. A thorough list of nonwoven manufacturing processes is described in "The Handbook of Nonwovens" edited by S. J. Russell and published by Woodhead Publishing Limited and CRC Press LLC (ISBN: 978-0-8493-2596-0), for example.

Direct Polymer to Wet-Laid Nonwoven Materials

Continuous and discontinuous fiber spinning technologies of molten materials and typically of thermoplastics are commonly referred to as meltspinning or spunmelt technologies. Spunmelt technologies may comprise both the meltblowing process and the spunbonding processes. A spunbonding process comprises supplying a molten polymer, which is then extruded via a die under pressure through a large number of orifices in a plate known as a spinneret. The resulting continuous fibers are quenched and drawn by any of a number of methods, such as slot draw systems, attenuator guns, or drawing rolls (Godet), for example. In the spunlaying or spunbonding process, the continuous fibers are collected as a loose web upon a moving foraminous surface, such as a wire mesh conveyor belt, for example. When more than one spinneret is used in line for forming a multi-layered nonwoven substrate, the subsequent nonwoven layers are collected upon the uppermost surface of the previously formed nonwoven layer. Spunlaid or spunbond nonwoven substrates may be multi-component (e.g., like a core and a sheath, or a segmented pie or islands-in-the-sea), multi-constituent (i.e., blends of multiple chemicals in one component), as well as have a variety of cross-sections besides round or circular, such as tri-lobal, oval or hollow. Examples of manufacturing such a wide range of spunlaid layers or fabrics are described in U.S. Pat. No. 3,502,763 to Hartmann et al., U.S. Pat. No. 3,692,618 to Dorschner et al., U.S. Pat. No. 3,338,992 to Kinney, U.S. Pat. No. 4,820,142 to Balk, U.S. Pat. No. 5,460,500 to Geus et al., U.S. Pat. No. 6,932,590 to Geus et al., U.S. Pat. No. 5,382,400 to Pike et al., U.S. Pat. No. 7,320,581 to Allen et al., and U.S. Pat. No. 7,476,350 to Allen.

The meltblowing process is related to the spunlaying or spunbonding process by forming a layer of a nonwoven substrate, wherein a molten polymer is extruded through orifices in a spinneret or a die, typically with a single row of small orifices in the die. A high flow rate of hot, high velocity gas impinges upon and attenuates the fibers as they exit the die, and quickly draws them to micro-fibers of diameters on the order of one to ten micrometers and of indeterminate length. This differs from the spunbonding process where the continuity of the fibers is generally preserved. The fibers are then blown and deposited by the high velocity air onto a collector, conveyor, or other web. Often meltblown nonwoven layers are added to spunlaid nonwoven layers to form spunbond-meltblown ("SM") nonwoven substrates or spunbond-meltblown-spunbond ("SMS") nonwoven substrates, which combine the attributes of S and M nonwoven structures, e.g., strong nonwoven substrates with some barrier properties. Descriptions for making such meltblown fibers, layers, and nonwoven substrates can be found for example in: "Superfine Thermoplastic Fibers", by Van A. Wente, in Ind. Eng. Chem. Res. 48 (8) 1956, pp. 1342-46, or in U.S. Pat. No. 3,849,241 to Buntin et al. and U.S. Pat. No. 5,098,636 to Balk.

Other methods to produce even finer fibers, including fibers with average diameters less than one micron or 1000 nanometers (an "N-fiber"), may comprise melt fibrillation, advanced meltblowing technology, or electrospinning Advanced melt-blowing technology is described, for example, in U.S. Pat. No. 4,818,464 to Lau, U.S. Pat. No. 5,114,631 to Nyssen et al., U.S. Pat. No. 5,620,785 to Watt et al., and U.S. Pat. No. 7,501,085 to Bodaghi et al. Melt film fibrillation technology, as example of melt fibrillation, is a general class of making fibers defined in that one or more polymers are molten and are extruded into many possible configurations (e.g., hollow tubes of films, sheets of films, co-extrusion, homogeneous or bicomponent films or filaments) and then fibrillated or fiberized into filaments. Examples of such processes are described in U.S. Pat. No. 4,536,361 to Torobin, U.S. Pat. No. 6,110,588 to Perez et al., U.S. Pat. No. 7,666,343 to Johnson et al., U.S. Pat. No. 6,800,226 to Gerking Electrospinning processes useful to make fine fibers are described in U.S. Pat. No. 1,975,504 to Formhals et al., U.S. Pat. No. 7,585,437, to Jirsak et al., U.S. Pat. No. 6,713,011 to Chu et al., U.S. Pat. No. 8,257,641 to Qi et al.; and also in "Electrospinning", by A. Greiner and J. Wendorff, in *Angew. Chem. Int. Ed.*, 2007, 46(30), 5670-5703.

The spunlaid or spunbond fibers typically have an average diameter in the range of about 8 microns to about 30 microns, or a fiber titer in the range from 0.5 to 10 denier. The meltblown fibers have a diameter of typically in the range from 0.5 microns to 10 microns on average, or 0.001 denier to 0.5 denier, and range from about 0.1 microns to over 10 microns. Fine fibers range in average or median diameter from 0.1 microns to 2 microns, and some fine fibers have a number-average diameter of less than about 1 micron, a mass-average diameter of less than about 1.5 microns, and a ratio of the mass-average diameter to the number-average diameter less than about 2.

Often meltblown nonwoven layers ("M") are added to spunlaid nonwoven layers ("S") to form spunbond-meltblown ("SM") nonwoven substrates, spunbond-meltblown-spunbond ("SMS") nonwoven substrates, SSMMS nonwoven substrates, SSMMSS nonwoven substrates, or other nonwoven substrates, which combine the attributes of S and M nonwoven structures, e.g., strong nonwoven substrates with some fluid barrier properties. The same can be done with fine fibers and layers of fine fibers, denominated "N", to make SN, MN, SMN, SMNS, SMNMS, SNMN, SSMNS, SSMNNS, or other suitable combinations of layers.

Dry-Laid and Wet-Laid Nonwoven Substrates

In addition to nonwoven substrates made from the fiber spinning technologies of molten materials, nonwoven substrates may be made by other means from pre-formed fibers (including natural fibers), such as by drylaid or wetlaid technologies. Drylaid technologies include carding and airlaying. These technologies may be combined with each other, e.g., drylaid with meltspun, to form multi-layer, functional nonwoven substrates.

The carding process uses fibers cut into discrete lengths called staple fiber. The type of fiber and the desired end product properties determine the fiber length and denier. Typical staple fibers have a length in the range of 20 mm to 200 mm and a linear density in the range of 1 dpf to 50 dpf (denier per fiber), though staple fibers beyond this range have also been used for carding. The carding technology processes these staple fibers into a formed substrate. Staple fibers are typically sold in compressed bales that need to be opened to make uniform nonwoven substrates. This opening process may be done through a combination of bale opening, coarse opening, fine opening, or by a similar process. Staple fibers are often blended in order to mix different fiber types and/or to improve uniformity. Fibers may be blended by blending fiber hoppers, bale openers, blending boxes, or by similar methods. The opened and blended fibers are transported to a chute that deposits the fibers across the width of the card and with a density as uniform as practical in order to make a nonwoven substrate with the desired basis weight uniformity. The card contains a series of parallel rollers and/or fixed plates that are covered with metallic clothing, rigid sawtoothed wires with specific geometry that staple fibers are processed between. Carding takes place when fiber tufts transport between the tangent points of two surfaces that have a differential surface speed and opposing angle directions on the metallic clothing. Cards may have a single main cylinder to card with or multiple cylinders. Cards may have a single doffer or multiple doffers to remove the carded fibers and the cards may contain randomizing rollers or condenser rollers to reduce the highly isotropic orientation of the individual fibers in the web. The carding process may contain a single card or multiple cards in line with one another, where the fibers of a subsequent card are deposited on top of the fibers from a preceding card and thus can form multiple layers, e.g., of different fiber compositions. The orientation of these cards may be parallel to the downstream operation or perpendicular to the downstream operation by means of turning or crosslapping.

The airlaid process also uses fibers of discrete length, though these fibers are often shorter than the staple fibers used for carding. The length of fibers used in airlaying typically ranges from 2 mm to 20 mm, though lengths beyond this range may also be used. Particles may also be deposited into the fibrous structure during the airlaying process. Some fibers for airlaying may be prepared similarly as for carding, i.e., opening and blending as described above. Other fibers, such as pulp, may use mills, such as hammer mills or disc mills, to individualize the fibers. The various fibers may be blended to improve the uniformity of properties of the finished nonwoven substrate. The airlaying forming device combines external air and the fibers and/or particles so that the fibers and/or particles are entrained in the airsteam. After entrainment, the fibers and/or particles are collected as a loose web upon a moving foraminous surface, such as a wire mesh conveyor belt, for example. The airlaying process may contain a single airlaying forming device or multiple airlaying forming devices in line with one another, where the fibers and/or particles of the subsequent airlaying forming device are deposited on top of the fibers and/or particles from a preceding airlaying forming device, thereby allowing manufacture of a multi-layered nonwoven substrate.

Wet-laid nonwovens are made with a modified papermaking process and typically use fibers in the range of 2 mm to 20 mm, though lengths beyond this range have also been used. Some fibers for wetlaying may be prepared similarly as for carding, i.e., opening and blending as described above. Other fibers, such as pulp, may use mills, such as hammer mills or disc mills, to individualize the fibers. The fibers are suspended in water, possibly with other additives like bonding agents, and this slurry is typically added to a headbox from where it flows onto a wetlaid forming device to create a sheet of material. After initial water removal, the web is bonded and dried.

Bonding

Nonwoven substrates may be bonded (consolidated) by thermal, mechanical or chemical processes. With nonwoven substrates made from cellulosic materials, nonwoven substrates may be hydrogen bonded. Bonding is typically performed in line with the forming process, but may be performed off line as well. Thermal bonding includes calender bonding with smooth and/or patterned rolls and thru-air bonding with flat belt and/or drum surfaces. Mechanical bonding includes needlepunching, stitchbonding, and hydroentangling (also known as spunlacing). Chemical bonding includes adhesive, latex, and/or solvent application to the fibers by spraying, printing, foaming, or saturating, followed by drying and creating a useful nonwoven substrate of sufficient integrity. Other post-processing, like printing or coating, may follow. Afterwards the nonwoven substrates are wound into roll form, slit/rewound, packaged, and shipped for further processing and/or converting into end products.

Composition of Fibers and Filaments

In various embodiments, synthetic fibers of the nonwoven structures may be made of polyesters, including PET, PTT, PBT, and polylactic acid (PLA), and alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types by Kraton), polystyrenes, polyamides, PHA (polyhydroxyalkanoates) and e.g., PHB (polyhydroxubutyrate), and starch-based compositions including thermoplastic starch, for example. The constituents of the fibers may be derived from biological sources such as plant matter, such as for PLA or "bio-PE", for example. The above polymers may be used as homopolymers, copolymers, blends, and alloys thereof. In the various embodiments, natural fibers of the nonwoven structures may be made of, but not limited to, digested cellulose fibers from softwood (derived from coniferous trees), hardwood (derived from deciduous trees) or cotton, including rayons and cotton, fibers from Esparto grass, bagasse, kemp, flax, jute, kenaf, sisal, and other lignaceous and cellulose fiber sources. The fibers may comprise other constituents for color, strength, aging stability, odor control or other purposes, e.g. titanium-dioxide to reduce gloss and improve opacity.

A variety of mass-produced absorbent articles and articles of commerce employ nonwoven substrates, such as SMS substrates, in their manufacture. One of the largest users of these nonwoven substrates is the disposable diaper industry, the wipes industry, the cleaning substrate industry, and feminine care products industry.

The following description generally discusses a suitable absorbent core, a topsheet or liquid pervious layer, and a backsheet or liquid impervious that may be used in absorbent articles. The absorbent core may be positioned at least partially intermediate, or fully intermediate, the liquid pervious layer and the liquid impervious layer. Other products, such as sanitary napkins, cleaning substrates, and wipes are also within the scope of the present disclosure as will be discussed below.

Figure 2:
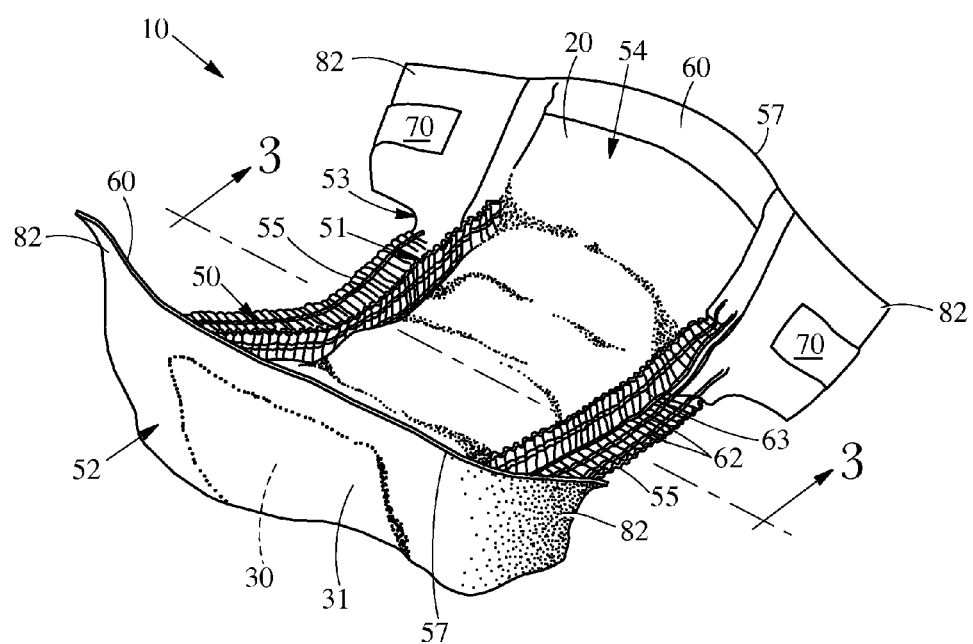
FIG. 2 is a perspective view of the absorbent article of FIG. 1 with the elastics in a relaxed/contracted state in accordance with a non-limiting embodiment.

FIG. 1 is a plan view of an absorbent article 10 that may have the nonwoven substrates of the present disclosure as a component thereof. The absorbent article 10 is illustrated in its flat, uncontracted state (i.e., with its elastic induced contraction removed for illustration) and with portions of the absorbent article 10 being cut-away to more clearly show the construction of the absorbent article 10. A portion of the absorbent article 10 which faces away from the wearer (i.e., the garment-facing surface) is oriented towards the viewer in FIG. 1. FIG. 2 is a perspective view of the absorbent article 10 of FIG. 1 in a partially contracted state. As shown in FIG. 1, the absorbent article 10 may comprise a liquid pervious topsheet 20, a liquid impervious backsheet 30 joined with the topsheet 20, and an absorbent core 40 positioned at least partially, or fully, intermediate the topsheet 20 and the backsheet 30. The absorbent core 40 has an exterior surface (or garment-facing surface) 42, an interior surface (or a wearer-facing surface) 44, side edges 46, and waist edges 48. In an embodiment, the absorbent article 10 may comprise gasketing barrier cuffs 50 and longitudinal barrier cuffs 51. The longitudinal barrier cuffs 51, in some embodiments, may extend generally parallel to a central longitudinal axis 59. For example, the longitudinal barrier cuffs 51 may extend substantially between the two end edges 57. The absorbent article 10 may comprise an elastic waist feature multiply designated as 60 and a fastening system generally multiply designated as 70.

In an embodiment, the absorbent article 10 may have an outer surface 52 (garment-facing surface), an inner surface 54 (wearer-facing surface) opposed to the outer surface 52, a first waist region 56, a second waist region 58, and a periphery 53 which is defined by longitudinal edges 55 and the end edges 57. (While the skilled artisan will recognize that an absorbent article, such as a diaper, is usually described in terms of having a pair of waist regions and a crotch region between the waist regions, in this application, for simplicity of terminology, the absorbent article 10 is described as having only waist regions comprising a portion of the absorbent article which would typically be designated as part of the crotch region). The inner surface 54 of the absorbent article 10 comprises that portion of the absorbent article 10 which is positioned adjacent to the wearer's body during use (i.e., the inner surface 54 is generally formed by at least a portion of the topsheet 20 and other components that may be joined to the topsheet 20). The outer surface 52 comprises that portion of the absorbent article 10 which is positioned away from the wearer's body (i.e., the outer surface 52 is generally formed by at least a portion of the backsheet 30 and other components that may be joined to the backsheet 30). The first waist region 56 and the second waist region 58 extend, respectively, from the end edges 57 of the periphery 53 to the lateral centerline (cross-sectional line 3-3) of the absorbent article 10.

Figure 3A:
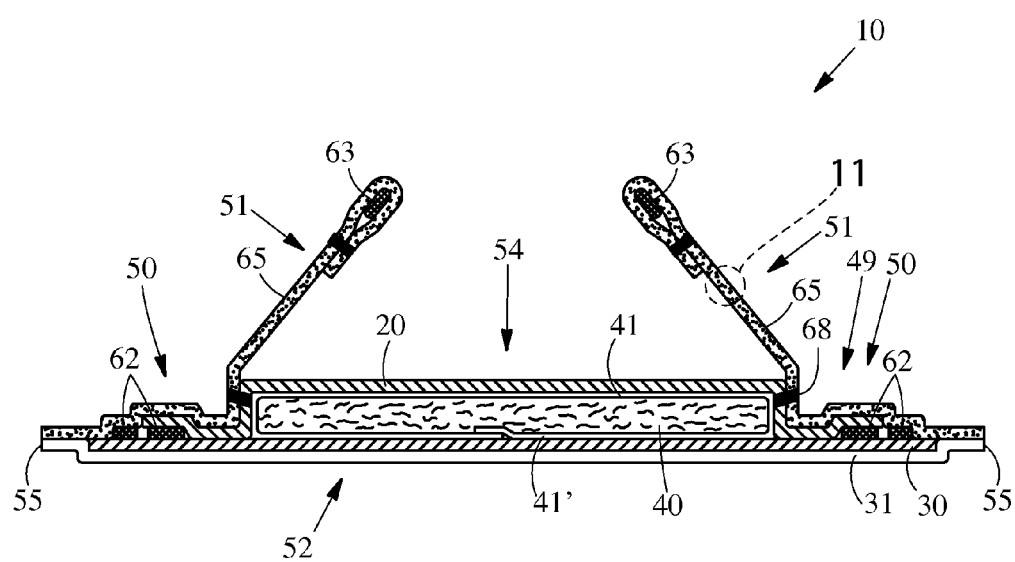
FIG. 3 is a cross-sectional view of the absorbent article of FIG. 1 taken along line 3-3 in accordance with a non-limiting embodiment.

FIG. 2 shows a perspective view of the absorbent article 10 (with elastics contracted) that comprises a pair of longitudinal barrier cuffs 51 in accordance with an embodiment of the present disclosure. FIG. 3 depicts a cross-sectional view taken along line 3-3 of FIG. 1.

In an embodiment, the absorbent core 40 may take on any size or shape that is compatible with the absorbent article 10. In an embodiment, portions of the absorbent core 40 may be manufactured from one or more of the nonwoven substrates of the present disclosure. In an embodiment, the absorbent article 10 may have an asymmetric, modified T-shaped absorbent core 40 having a narrowing of the side edge 46 in the first waist region 56, but remaining generally rectangular-shaped in the second waist region 58. The absorbent core may also have any other suitable shapes, such as rectangular. Various absorbent core constructions are generally known in the art. The absorbent core 40 may also comprise a core cover 41 (as shown in FIG. 3 and as described in greater detail below) and a nonwoven dusting layer 41' that is disposed between the absorbent core 40 and the backsheet 30. In an embodiment, the core cover 41 and the nonwoven dusting layer 41' may be manufactured from one or more of the nonwoven substrates of the present disclosure.

The core 40 may be a C-wrapped core or other suitable core configuration. In a C-wrapped core, the core cover 41 may be wrapped at least partially around the dusting layer 41', or vice versa, to seal the core 40 and prevent, or at least inhibit, its contents from escaping from the core 40 after it has been insulted with bodily fluids. In an embodiment, the core may comprise superabsorbent polymers in a percentage by weight of at least 80%, at least 85%, at least 90%, at least 95% or even 100%.

In an embodiment, the topsheet 20 of the absorbent article 10 may comprise a hydrophilic material that promotes rapid transfer of fluids (e.g., urine, menses, and/or runny feces) through the topsheet 20. The topsheet 20 may be pliant, soft feeling, and non-irritating to the wearer's skin. Further, the topsheet 20 may be fluid pervious, permitting fluids (e.g., menses, urine, and/or runny feces) to readily penetrate through its thickness. In an embodiment, the topsheet 20 may be made of a hydrophilic material or at least the upper surface of the topsheet may be treated to be hydrophilic so that fluids will transfer through the topsheet more rapidly and enter the absorbent core 40. This diminishes the likelihood that body exudates or fluids will flow off of the topsheet 20 rather than being drawn through the topsheet 20 and being absorbed by the absorbent core 40. The topsheet 20 may be rendered hydrophilic by treating it with a surfactant, for example. In an embodiment, the topsheet 20 may be manufactured from one or more of the nonwoven substrates of the present disclosure.

In an embodiment, the backsheet 30 may be impervious, or at least partially impervious, to fluids or low surface tension fluids (e.g., menses, urine, and/or runny feces). The backsheet 30 may be manufactured from a thin plastic film, although other flexible fluid impervious materials may also be used. The backsheet 30 may prevent, or at least inhibit, the bodily exudates absorbed and contained in the absorbent core 40 from wetting articles which contact the absorbent article 10, such as bedsheets, clothing, pajamas, and undergarments, for example. The backsheet 30 may comprise a woven or a nonwoven substrate, polymeric films such as thermoplastic films of polyethylene or polypropylene, and/or composite materials such as a film-coated nonwoven material or a film-nonwoven laminate. In an embodiment, a backsheet 30 may be a polyethylene film having a thickness of from 0.012 mm (0.5 mils) to 0.051 mm (2.0 mils). Example polyethylene films are manufactured by Clopay Corporation of Cincinnati, Ohio, under the designation P18-1401 and by Tredegar Film Products of Terre Haute, Ind., under the designation XP-39385.

The backsheet 30 may be embossed and/or matte finished to provide a more cloth-like appearance. Further, the backsheet 30 may permit vapors to escape from the absorbent core 40 (i.e., the backsheet 30 is breathable and has an adequate air permeability), while still preventing, or at least inhibiting, bodily exudates from passing through the backsheet 30. The size of the backsheet 30 may be dictated by the size of the absorbent core 40 and the exact absorbent article design selected. In an embodiment, the backsheet 30 may be manufactured from one or more of the nonwoven substrates of the present disclosure.

Other optional elements of the absorbent article 10 may comprise a fastening system 70, elasticized side panels 82, and a waist feature 60. The fastening system 70 allows for the joining of the first waist region 56 to the second waist region 58 in an overlapping configuration such that lateral tensions are maintained around the circumference of the absorbent article 10 to maintain the absorbent article 10 on the wearer. Example fastening systems 70 are disclosed in U.S. Pat. No. 4,846,815, issued to Scripps, on Jul. 11, 1989, U.S. Pat. No. 4,894,060, issued to Nestegard, on Jan. 16, 1990, U.S. Pat. No. 4,946,527, issued to Battrell, on Aug. 7, 1990, U.S. Pat. No. 3,848,594, issued to Buell, on Nov. 19, 1974, U.S. Pat. No. 4,662,875, issued to Hirotsu et al., on May 5, 1987, and U.S. Pat. No. 5,151,092, issued to Buell et al., on Sep. 29, 1992. In certain embodiments, the fastening system 70 may be omitted. In such embodiments, the waist regions 56 and 58 may be joined by the absorbent article manufacturer to form a pant-type diaper having a preformed waist opening and leg openings (i.e., no end-user manipulation of the diaper is needed to form the waist opening and leg openings). Pant-type diapers are also commonly referred to as "closed diapers," "prefastened diapers," "pull-on diapers," "training pants," and "diaper-pants". Suitable pants-type diapers are disclosed in U.S. Pat. No. 5,246,433, issued to Hasse et al., on Sep. 21, 1993, U.S. Pat. No. 5,569,234, issued to Buell et al., on Oct. 29, 1996, U.S. Pat. No. 6,120,487, issued to Ashton, on Sep. 19, 2000, U.S. Pat. No. 6,120,489, issued to Johnson et al., on Sep. 19, 2000, U.S. Pat. No. 4,940,464, issued to Van Gompel et al., on Jul. 10, 1990, and U.S. Pat. No. 5,092,861, issued to Nomura et al., on Mar. 3, 1992. Generally, the waist regions 56 and 58 may be joined by a permanent or refastenable bonding method.

In an embodiment, the absorbent article 10 may comprise one or more longitudinal barrier cuffs 51 which may provide improved containment of fluids and other body exudates. The longitudinal barrier cuffs 51 may comprise one or more of the nonwoven substrates of the present disclosure. The longitudinal barrier cuffs 51 may also be referred to as leg cuffs, barrier leg cuffs, longitudinal leg cuffs, leg bands, side flaps, elastic cuffs, or "stand-up" elasticized flaps. Elasticity may be imparted to the longitudinal barrier cuffs 51 by one or more elastic members 63. Elastic members 63 may provide elasticity to the longitudinal barrier cuff 51 and may aid in keeping longitudinal barrier cuff 51 in a "stand-up" position. U.S. Pat. No. 3,860,003, issued to Buell, on Jul. 14, 1975, describes a disposable diaper that provides a contractible leg opening having a side flap and one or more elastic members to provide an elasticized leg cuff. U.S. Pat. Nos. 4,808,178 and 4,909,803 issued to Aziz et al. on Feb. 28, 1989 and Mar. 20, 1990, respectively, describe absorbent articles comprising "stand-up" elasticized flaps that improve the containment at the leg regions of the absorbent article 10. Additionally, in some embodiments, the one or more longitudinal barrier cuffs 51 may be integral with one or more gasketing cuffs 50. As with the longitudinal barrier cuffs 51, the gasketing cuffs 50 may comprises one or more elastic members 62. The gasketing cuffs 50 may comprise one or more nonwoven substrates of the present disclosure.

FIG. 3 illustrates a cross-sectional view of the absorbent article 10 of FIG. 1 taken along line 3-3. FIG. 3 depicts one cuff construction; however, modifications may be made to the cuff construction without departing from the spirit and scope of the present disclosure. A gasketing cuff 50 and a longitudinal barrier cuff 51 are both shown in FIG. 3, but a single cuff design is also feasible. FIG. 3 illustrates a gasketing cuff 50 and a longitudinal barrier cuff 51 construction in accordance with one embodiment. Both cuffs 50, 51 may share a common nonwoven substrate 65, such as an SMS nonwoven substrate, an SNS nonwoven substrate, or an SMNS nonwoven substrate, for example. The longitudinal barrier cuff 51 is shown in a single layer configuration where over a substantial portion of the lateral width of the longitudinal barrier cuff 51 comprises a single ply of the nonwoven substrate 65. Those of skill in the art will recognize that the exact configuration of the nonwoven substrate may be altered in various embodiments.

As shown in FIG. 3, a core cover 41 may be included in certain embodiments of the absorbent article 10 to provide structural integrity to the absorbent core 40. The core cover 41 may contain the absorbent core 40 components such as cellulosic material and absorbent gelling material or superabsorbent polymers, which both may tend to migrate, move, or become airborne without a physical barrier. The core cover 41 may entirely envelop the core 40, as shown in FIG. 3, or may partially cover the absorbent core 40.

In certain embodiments, the absorbent article 10 may comprise an outer cover 31. The outer cover 31 may cover all of, or substantially all of, the exterior surface of the absorbent article 10. In some embodiments, the outer cover 31 may be coterminous with the backsheet 30. The outer cover 31 may be bonded to a portion of the backsheet 30 to form a laminate structure.

Figure 4:
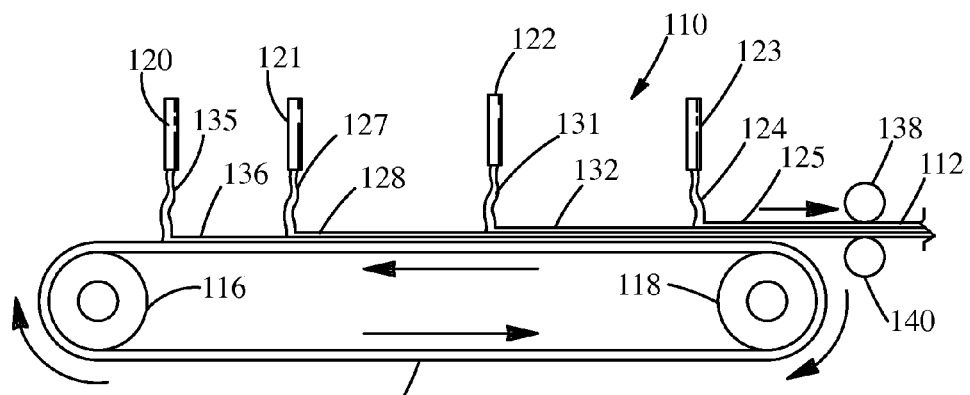
FIG. 4 is a schematic diagram of a forming machine used to make a nonwoven substrate in accordance with a non-limiting embodiment.

FIG. 4 illustrates a schematic diagram of a forming machine 110 used to make a nonwoven substrate 112 of the present disclosure. To make a nonwoven substrate, the forming machine 110 is shown as having a first beam 120 for producing first coarse fibers 135 (e.g., spunbond fibers), an optional second beam 121 for producing intermediate fibers 127 (e.g., meltblown fibers), a third beam 122 for producing fine fibers 131 (e.g., N-fibers), and a fourth beam 123 for producing second coarse fibers 124 (e.g., spunbond fibers). The forming machine 110 may comprise an endless forming belt 114 which travels around rollers 116, 118 so the forming belt 114 is driven in the direction as shown by the arrows 114. In various embodiments, if the optional second beam 121 is utilized, it may be positioned intermediate the first beam 120 and the third beam 122 (as illustrated), or may be positioned intermediate the third beam 122 and the fourth beam 124, for example. Rolls 138 and 140 may form a nip to bond or calender bond the fibers in the multiple layers together to form the nonwoven substrate. Element 136 may be a layer of spunbond fibers. Element 128 may be a layer of intermediate fibers, spunbond fibers, or fine fibers. Element 132 may be a layer of intermediate fibers, spunbond fibers, or fine fibers. Element 125 may be a layer of spunbond fibers. Each of the layers of fibers may be formed to grow fibrils extending outwardly therefrom after a predetermined period of time under ambient conditions, as discussed in further detail below.

Figure 5:
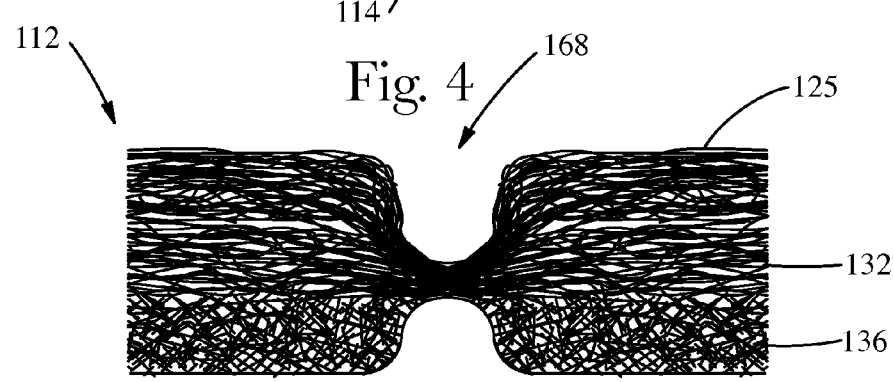
FIG. 5 is an example cross-sectional view of a nonwoven substrate in a three layer configuration in accordance with a non-limiting embodiment.

FIG. 5 illustrates a cross-sectional view of an SNS nonwoven substrate or an SMS nonwoven substrate at a calender bond site 168 in accordance with an embodiment. Fibrils may grow out of the calender bond site 168 after a predetermined period of time under ambient conditions, as discussed below. The spunbond, intermediate, and fine fibers may be of single component or bicomponent or polymer blend type.

Figure 6:
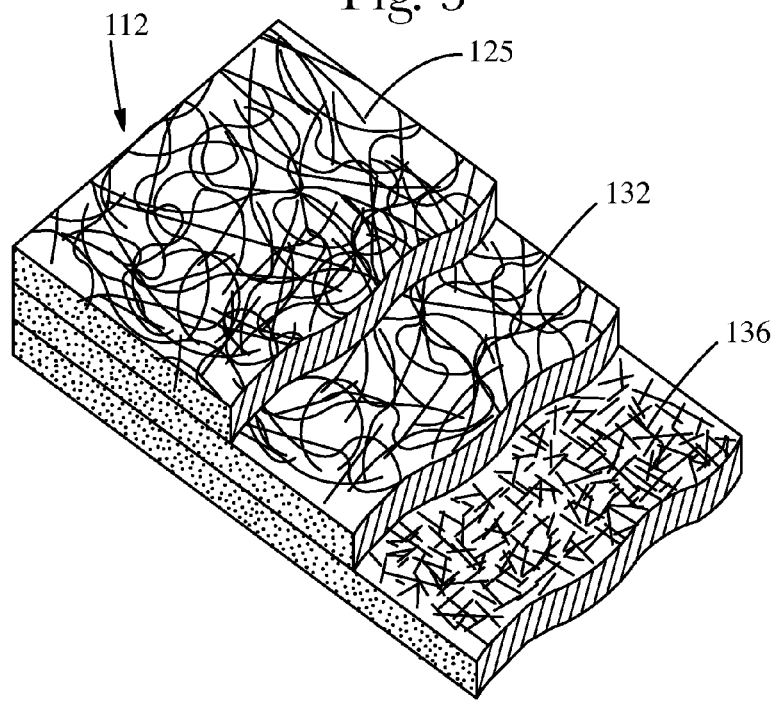
FIG. 6 is a perspective view of the nonwoven substrate of FIG. 5 with various portions of nonwoven layers cut away to show the composition of each nonwoven layer in accordance with a non-limiting embodiment.

In an embodiment, referring to FIGS. 5 and 6, the nonwoven substrate 112 may comprise a first nonwoven layer 125, a second nonwoven layer 132, and a third nonwoven layer 136. The bond site 168 may have a bond area. The second nonwoven layer 132 may be disposed intermediate the first nonwoven layer 125 and the third nonwoven layer 136. Also, the first nonwoven layer 125, the second nonwoven layer 132, and the third nonwoven layer 136 may be intermittently bonded to each other using any suitable bonding process, such as a calendering bonding process, for example. In an embodiment, the nonwoven substrate 112 does not comprise a film. In various embodiments, the nonwoven substrate 112 may comprise a spunbond layer, which may correspond to the first nonwoven layer 125, an N-fiber layer or intermediate layer, which may correspond to the second nonwoven layer 132, and a second spunbond layer, which may correspond to the third nonwoven layer 136.

Figure 7:
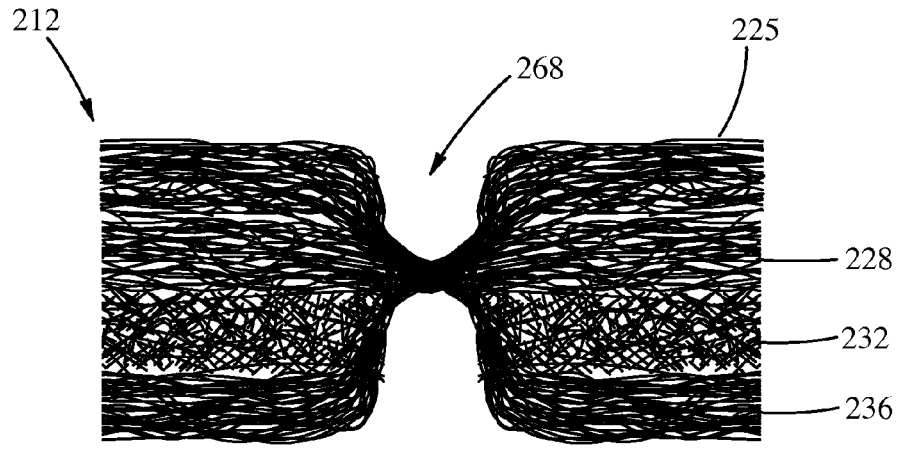
FIG. 7 is a cross-sectional view of a nonwoven substrate in a four layer configuration in accordance with a non-limiting embodiment.
Figure 8:
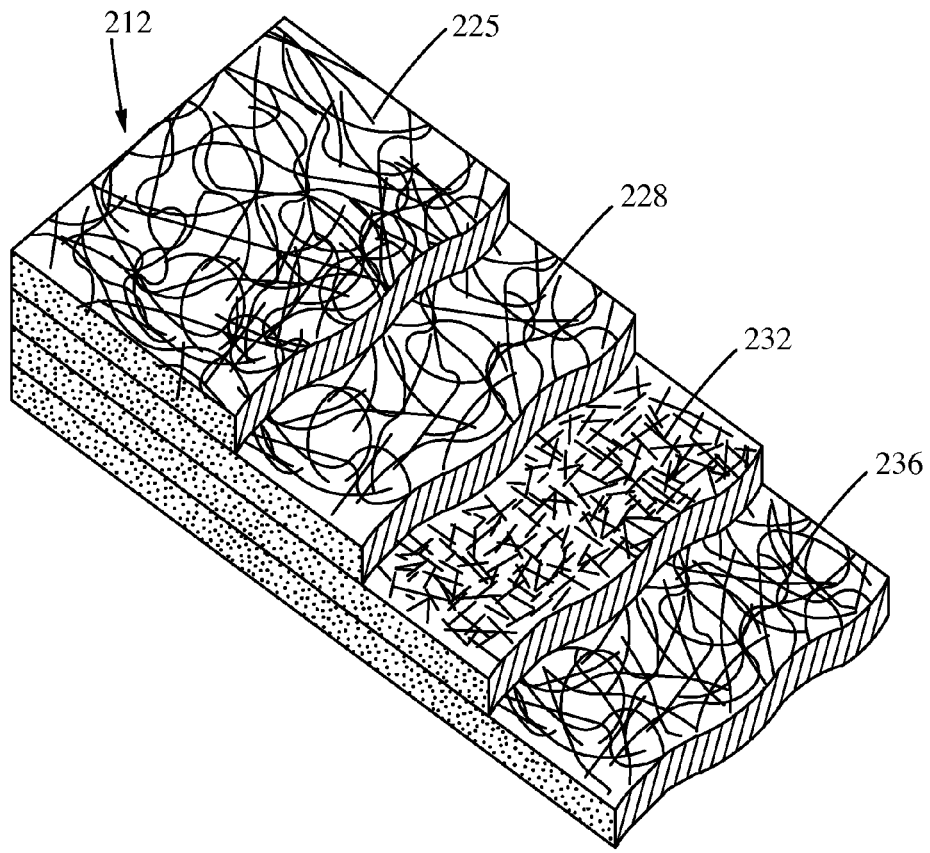
FIG. 8 is a perspective view of the nonwoven substrate of FIG. 7 with various portions of nonwoven layers cut away to show the composition of each nonwoven layer in accordance with a non-limiting embodiment.

In an embodiment, referring to FIGS. 7 and 8, a nonwoven substrate 212 may comprise a first nonwoven layer 225, a second nonwoven layer 232, a third nonwoven layer 236, and a fourth nonwoven layer 228. A bond site 268, such as a calender bond site, is illustrated in the nonwoven substrate 212. The bond site 268 has a bond area. The first nonwoven layer 225, the second nonwoven layer 232, the third nonwoven layer 236, and the fourth nonwoven layer 228 may be intermittently bonded to each other using any suitable bonding process, such as a calendering bonding process, for example. In an embodiment, the nonwoven substrate 212 does not comprise a film. In various embodiments, the nonwoven substrate 212 may comprise a spunbond layer, which may correspond to the first nonwoven layer 225, a meltblown layer or fine fiber layer, which may correspond to the fourth nonwoven layer 228, a fine or N-fiber layer or a meltblown layer, which may correspond to the second nonwoven component layer 232 and a second spunbond layer, which may correspond to the third nonwoven component layer 236. Other configurations of nonwoven substrates are envisioned and are within the scope of the present disclosure, such as a nonwoven substrate comprising one or more spunbond layers, one or more meltblown or intermediate layers, and/or one or more fine or N-fiber layers, for example.

In an embodiment, the nonwoven substrates of the present disclosure may be formed of a plurality of nonwoven layers arranged in various combinations and permutations of a plurality of spunbond, meltblown, and N-fiber layers, including but not limited to SMS, SMMS, SSMMS, SMMSS, SMN, SNS, SMNMS, SMMNMS, SSMMNS, SSNNSS, SSSNSSS, SSMMNNSS, SSMMNNMS, and the other suitable variations.

Figure 9:
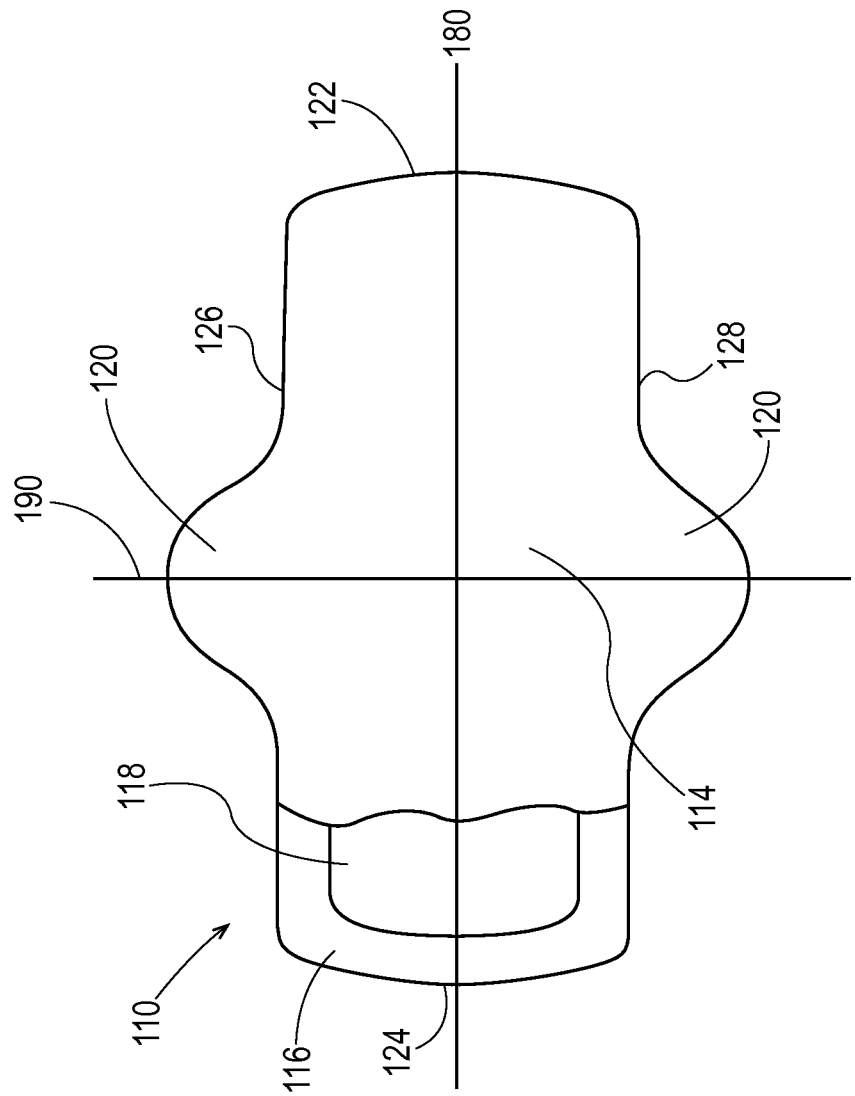
FIG. 9 is a top view of an absorbent article that is a sanitary napkin which may comprise the nonwoven substrates of the present disclosure in accordance with a non-limiting embodiment.

In an embodiment, referring to FIG. 9, the absorbent article may be a sanitary napkin 110. The wearer-facing surface is facing the viewer in FIG. 9. The sanitary napkin 110 may comprise a liquid permeable topsheet 114, a liquid impermeable, or substantially liquid impermeable, backsheet 116, and an absorbent core 118 positioned at least partially intermediate the topsheet 114 and the backsheet 116. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a rear edge 124 longitudinally opposing the front edge 122, a first side edge 126, and a second side edge 128 longitudinally opposing the first side edge 126. The longitudinal axis 180 may extend from a midpoint of the front edge 122 to a midpoint of the rear edge 124. The lateral axis 190 may extend from a midpoint of the first side edge 126 to a midpoint of the second side edge 128. The sanitary napkin 110 may also be provided with any additional features commonly found in sanitary napkins as is known in the art, such as an adhesive on the backsheet to apply the sanitary napkin to an undergarment, for example. The nonwoven substrates of the present disclosure may form one or more portions of the sanitary napkin 110, such as the topsheet 114, the backsheet 116, the absorbent core 118, and/or the wings 120, for example.

In an embodiment, a nonwoven substrate may comprise one or more layers of spunbond fibers "S", meltblown fibers "M", and/or fine fibers "N". One or more of the nonwoven layers may comprise fibers, wherein at least a plurality of the fibers, or all or most of the fibers, comprise fibrils extending outwardly or largely radially outwardly from a surface or a radial outer surface of the fibers. In an embodiment, the fibrils may be present in one layer of the nonwoven substrate (in all or some of the fibers), in all layers of the nonwoven substrate (in all or some of the fibers), or in less than all layers of the nonwoven substrate (in all or some of the fibers). In one instance, at least one layer of the nonwoven substrates of the present disclosure may have a plurality of fibers, or all fibers, that are free of fibrils, or substantially free of fibrils.

Figure 10:
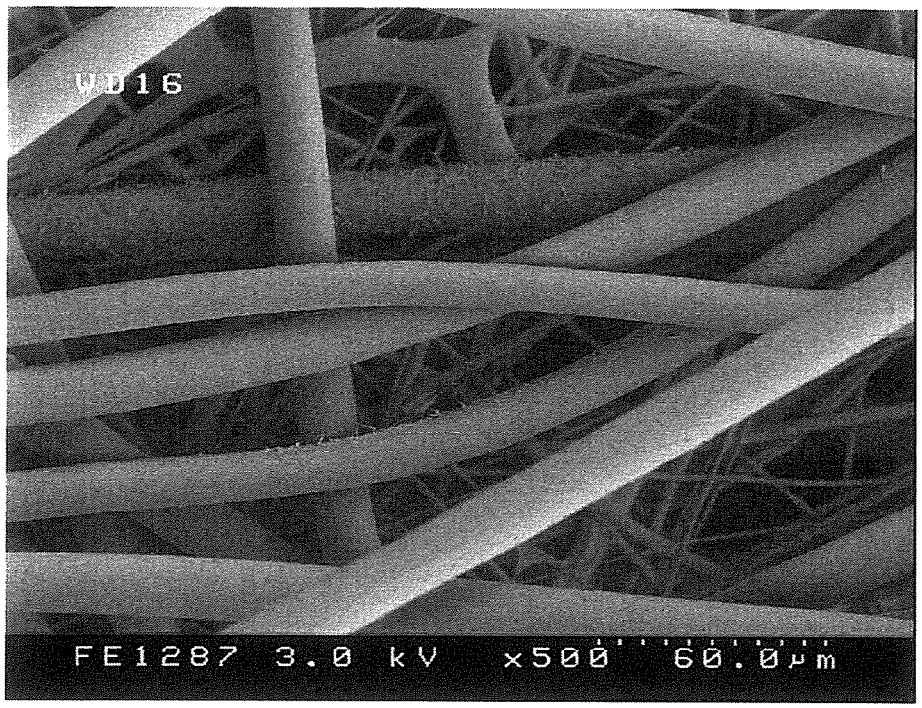
FIGS. 10-12 are scanning electron microscope ("SEM") photographs of a nonwoven substrate having fibrils in spunbond layers thereof in accordance with various non-limiting embodiments.
Figure 11:
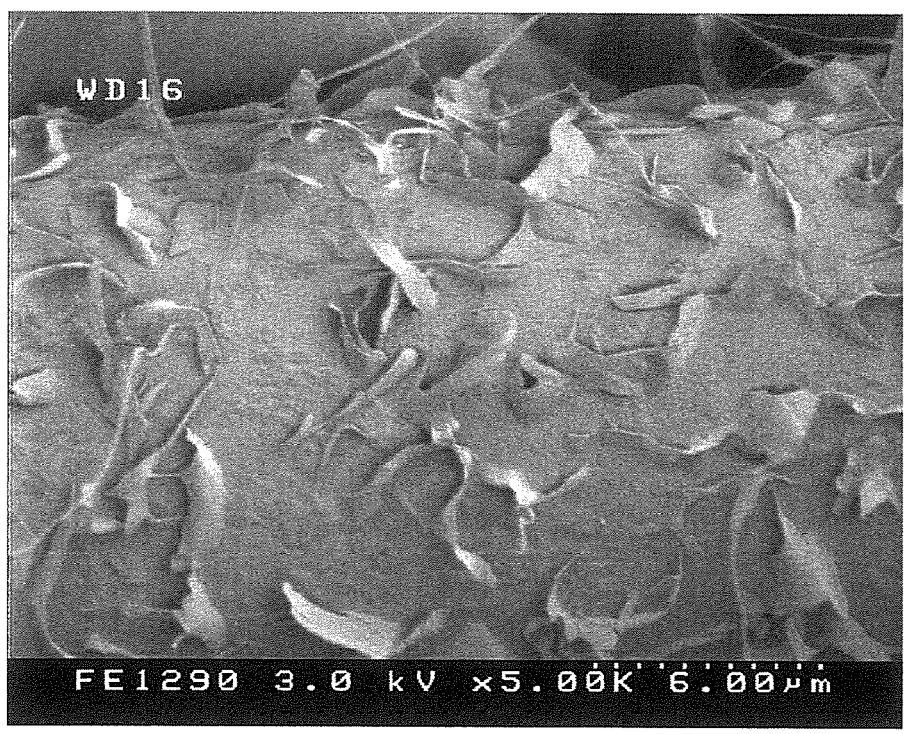
Figure 12:
Figure 13:
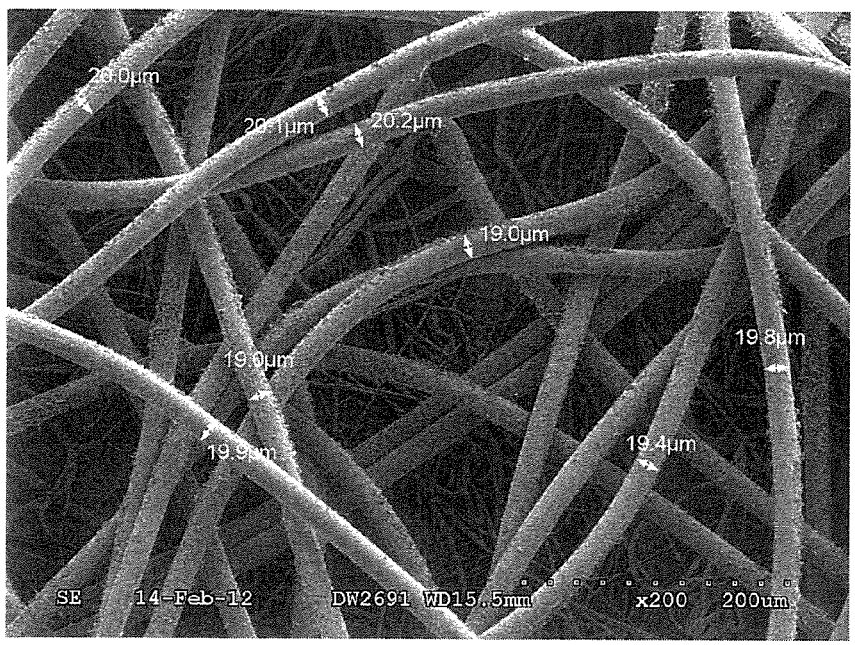
FIGS. 13-15 are additional SEM photographs of a nonwoven substrate having fibrils in spunbond layers thereof in accordance with various non-limiting embodiments.
Figure 14:
Figure 15:
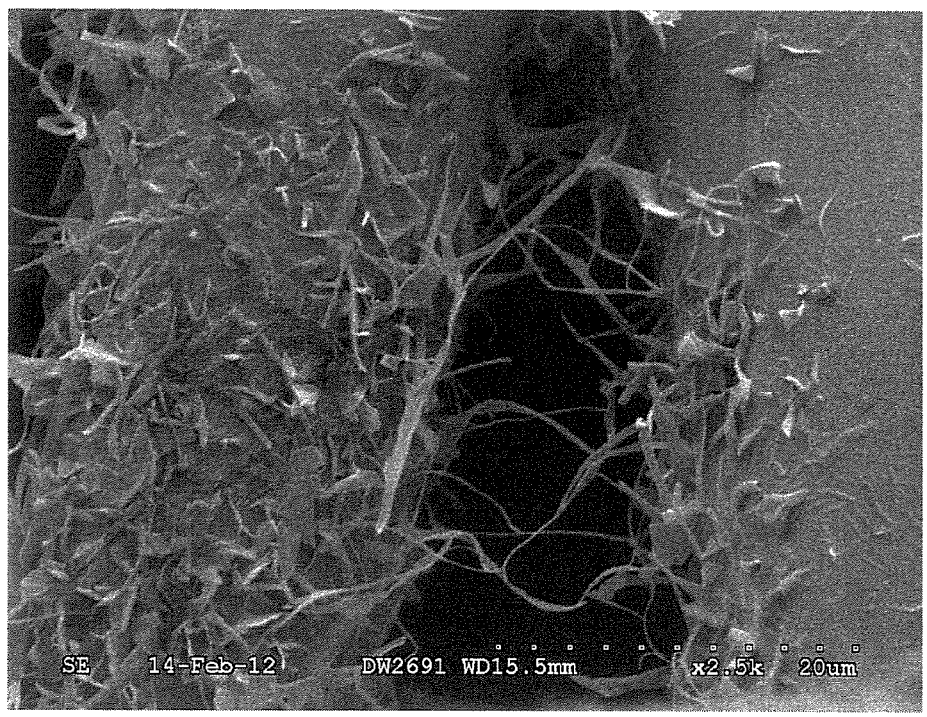

Scanning electron microscope photographs of nonwoven substrates having spunbond fibers comprising fibrils extending outwardly or radially outwardly from a surface thereof are illustrated in FIGS. 10-15. FIGS. 10-12 are of a 22 gsm SMMS nonwoven substrate, wherein the spunbond fibers of the nonwoven substrate were formed from a composition comprising about 10% of the lipid ester glycerol tristearate by weight of the composition. The spunbond layers of the nonwoven substrate each have a 10 gsm basis weight, while the meltblown layers each have a 1 gsm basis weight. The meltblown layers in FIGS. 10-12 do not have fibers comprising fibrils, although the meltblown fibers (and fine fibers) having fibrils is within the scope of the present disclosure. FIGS. 11 and 12 are more magnified views of the nonwoven substrate of FIG. 10. FIGS. 13-15 are of a 14 gsm SM nonwoven substrate, wherein the spunbond fibers of the nonwoven substrate were formed from a composition comprising 10% of the lipid ester glycerol tristearate by weight of the composition. FIGS. 14 and 15 are more magnified views of the nonwoven substrate of FIG. 13. The spunbond layer of the nonwoven substrate has a basis weight of 13 gsm and the meltblown layer has a basis weight of 1 gsm. The meltblown layers of FIGS. 13-15 do not have fibers comprising fibrils, although the meltblown fibers (and fine fibers) having fibrils is within the scope of the present disclosure.

Figure 16:
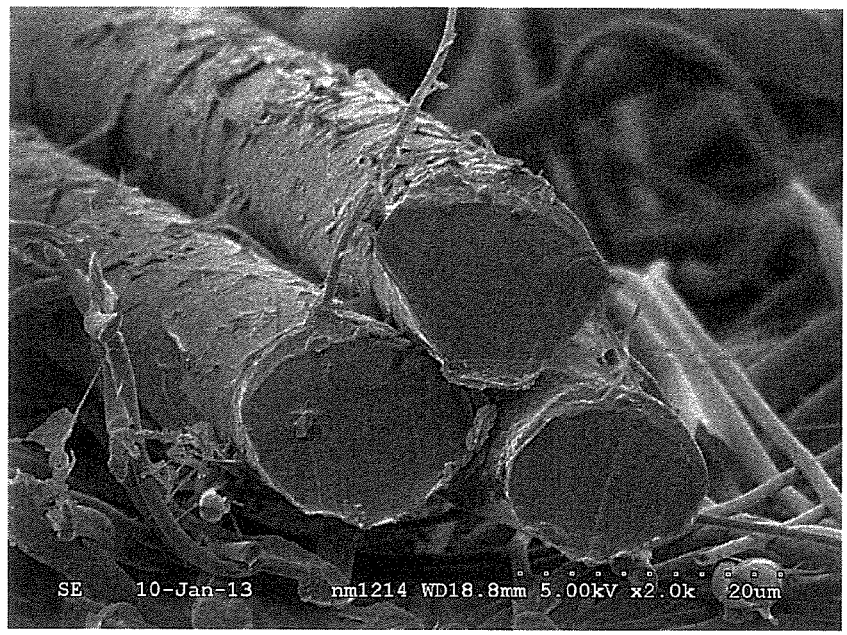
FIGS. 16-18 are SEM photographs of cross-sectional views of portions of a nonwoven substrate having fibrils in spunbond layers thereof in accordance with various non-limiting embodiments.
Figure 17:
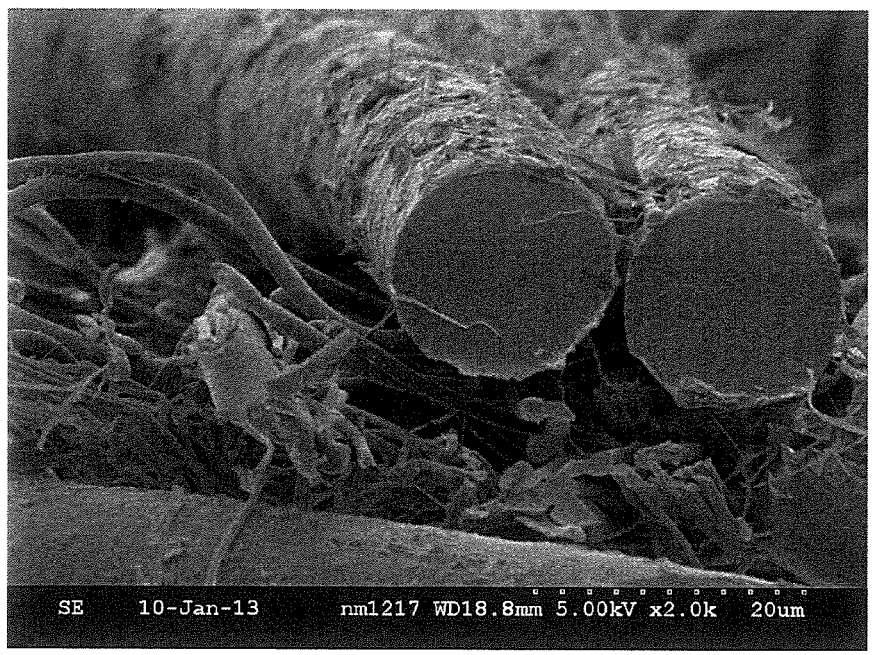
Figure 18:
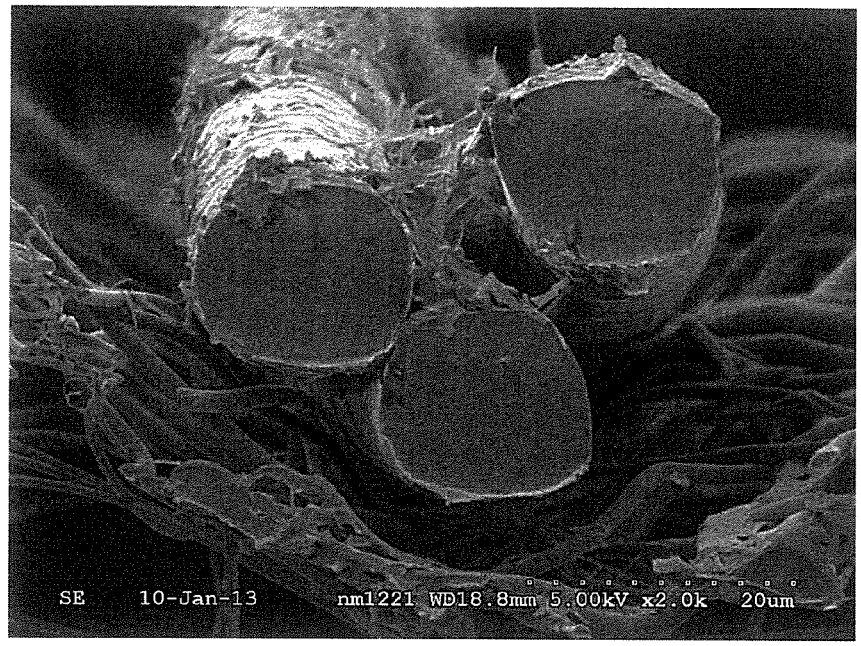

FIGS. 16-18 illustrate SEM photographs of cross-sectional views of an SMNS nonwoven substrate, wherein at least some of the spunbond fibers comprise fibrils. The nonwoven substrate has a total basis weight of 18 gsm. The spunbond fibers comprising fibrils are formed from a composition comprising 10% glycerol tristearate, by weight of the composition. The meltblown layer and the fine fiber layer do not have fibers comprising fibrils in FIGS. 16-18, although the meltblown and fine fibers having fibrils is within the scope of the present disclosure.

Some example configurations of nonwoven substrates having one or more layers having a plurality of fibers comprising fibrils, or all fibers comprising fibrils, are listed below. An "*" after the letter indicates that the layer has fibers, wherein at least some of, or all of, the fibers have fibrils. Some example configurations are as follows: S*MS*, SM*S, S*M*S, SM*S*, S*M*S*, S*M*NS, S*M*NS*, S*M*N*S*, SM*N*S, S*MNS*, SMN*S, S*SMNS, S*S*MNS, S*S*MNS*, S*S*M*NS*, S*S*M*N*S*, S*SM*NS*, S*MNMS*, S*M*NMS*, SSM*N*MS, S*S*M*MS, S*SM*MS, and/or S*MM*S. Any other suitable configurations of layers with or without fibrils are also within the scope of the present disclosure.

In some embodiments, it may be desirable for one or more layers comprising fibers comprising fibrils to be positioned on certain sides of the nonwoven substrate or at certain locations within the nonwoven substrate. In an example, the layers comprising the fibers comprising the fibrils may be positioned on a wearer-facing side or a garment-facing side or both of an absorbent article while the middle layers of the nonwoven substrate may or may not comprise fibers comprising fibrils. In other embodiments, the layers comprising the fibers comprising fibrils may be positioned in intermediate layers of the nonwoven substrate. In still other embodiments, the layers comprising fibers comprising fibrils may alternate through a nonwoven substrate (e.g., layer with fibers comprising fibrils, layer without fibers comprising fibrils, layer with fibers comprising fibrils etc.). In other embodiments, the layers with fibers comprising fibrils may be positioned in surface to surface contact with each other. The positioning of the layers comprising fibers comprising fibrils may be specific to particular applications. For a wipe, the layer or layers of fibers comprising fibrils may be positioned on the side of the wipe that will contact the surface or body part to be cleaned, wiped, rubbed, or scrubbed or may be positioned at other locations.

While the fibrils extend outwardly from surfaces of individual fibers, the fibrils may also extend to (i.e., contact) other fibers within the same layer or a different layer of a nonwoven substrate and/or to fibrils extending from fibers within the same layer or a different layer of the nonwoven substrate. An example of this feature is disclosed in FIGS. 14 and 15. When the fibrils extend between fibers and/or other fibrils, the nonwoven substrate may achieve a greater resistance to fluid penetration (e.g., low surface tension fluid strikethough) owing to the fibrils closing gaps or pores in the nonwoven substrate when engaged to other fibers or fibrils. Stated another way, the fibrils extending between the fibers and/or other fibrils reduce the open area of the nonwoven substrate, thereby increasing its fluid barrier properties. In some instance, longer fibrils may contact other fibrils and/or fibers more than shorter fibrils.

In various embodiments, the fibrils may have a length, from an outer surface, or a radial outer surface, of the fibers to a free end of the fibrils (i.e., the end of the fibrils most distal from the outer surface of the fibers), in the range of about 0.2 μm to about 40 μm, about 0.5 μm to about 20 μm, about 1 μm to about 15 μm, about 1 μm to about 10 μm, about 1 μm to about 5 μm, about 2.5 μm to about 5 μm, about 2 μm to about 4 μm, about 2.5 μm to about 3.5 μm, or about 3 μm, specifically reciting all 0.1 μm increments within the above-referenced ranges and all ranges formed therein or thereby. The fibrils of the various fibers in the one or more nonwoven layers may be the same length or within the same range of lengths, substantially the same length or within substantially the same range of lengths, or may have different lengths or different ranges of lengths. In an embodiment, the fibers in a layer of a nonwoven substrate, such as a spunbond layer, may have fibers having fibrils with a first length or range of lengths and the fibers in a second layer of the nonwoven substrate, such as another spunbond layer, a meltblown layer, or a fine fiber layer, may have fibers having fibrils with a second length or range of lengths. The first and second lengths and/or ranges of lengths of the fibrils may be the same, substantially the same, or different. In an embodiment, the first and second lengths and/or ranges of lengths of the fibrils may be smaller or larger in the meltblown layer(s) or fine fiber layer(s) than in the spunbond layer(s). Furthermore, the first and second lengths and/or ranges of lengths of the fibrils may be smaller or larger in the fine fiber layer(s) than in the meltblown layer(s). The fibrils may have a uniform thickness or a varying thickness and may have any suitable cross-sectional shape. It is believed that one key factor that determines the length, thickness, and/or cross-sectional shape of the fibrils is the amount, by weight of the composition, of melt additives, such as lipid esters, added to a composition used for forming the fibers, as will be discussed in further detail below. Similarly important is the selection of the bulk polymer composition into which the melt additive is inserted and out of which the fibrils emerge, more specifically, the hardness, density, and crystallinity of the bulk polymer matrix in the fibers is a factor. Another factor is the composition of the melt-additive, e.g., the specific type of lipid ester such that it can diffuse through the bulk polymer matrix more or less easily and such that it can continue to grow as a fibril from surface of the fiber. Other factors affecting the length, thickness, and/or cross-sectional shape of the fibrils are environmental conditions, especially conditions significantly above or below ambient conditions. The length of the fibrils is measured according to the Fibril Length Measurement Test described below.

In various embodiments, the fibrils may have a cross-sectional shape that is not circular, but instead is generally elliptical or even close to being rectangular. It is therefore useful to describe the cross-sectional size ("thickness" or "width") of the fibrils in terms of hydraulic diameter. The hydraulic diameter is determined by calculating the cross-sectional area (taken somewhere in the center ⅓ of the length of the fibril), multiplied by 4, and divided by the perimeter of the cross-sectional shape. Hydraulic Diameter $D_H=4*Area/Perimeter$. For a fibril having a circular-shaped cross-section, the hydraulic diameter is equal to the diameter of the fibril, and for a fibril having a rectangular-shaped cross-section, the hydraulic diameter, $D_H=4*L*W/(2*L+2*W)$ with L and W being the rectangular sides of the cross-section, so that a fibril with cross-sectional dimensions of 300 nm (W) and 1500 nm (L) has a hydraulic diameter of 500 nm. Approximations for perimeters of other cross-sectional shapes can be calculated according to known mathematical formulas.

In various embodiments, the average hydraulic diameter (i.e., cross-sectional thickness) of the fibrils may be in the range of about 50 nm to about 1100 nm, about 100 nm to about 800 nm, about 200 nm to about 800 nm, about 300 nm to about 800 nm, about 500 nm to about 800 nm, about 100 nm to about 500 nm, or about 600 nm, specifically reciting all 1 nm increments within the above-referenced ranges and all ranges formed therein or thereby. The hydraulic diameter of an individual fibril may be constant, substantially constant or variable about the fibril's length. In an embodiment, the hydraulic diameter of a fibril may decrease about the length of the fibril (from the beginning end of the fibril to its most distal end). In an embodiment, the fibers in a layer of a nonwoven substrate, such as a spunbond layer, may have fibers having fibrils with a first average hydraulic diameter or range of average hydraulic diameters and the fibers in a second layer of the nonwoven substrate, such as a meltblown layer or a fine fiber layer, may have fibers having fibrils with a second average hydraulic diameter or range of average hydraulic diameters. The first and second average hydraulic diameters and/or ranges of average hydraulic diameters of the fibrils may be the same, substantially the same, or different. In an embodiment, the first and second average hydraulic diameters and/or ranges of average hydraulic diameters of the fibrils may be smaller, larger, or the same in the meltblown layers or fine fiber layers than in the spunbond layer or layers. Furthermore, the first and second average hydraulic diameters and/or ranges of average hydraulic diameters of the fibrils may be smaller, larger, or the same in the fine fiber layers than in the meltblown layers.

Figure 19:
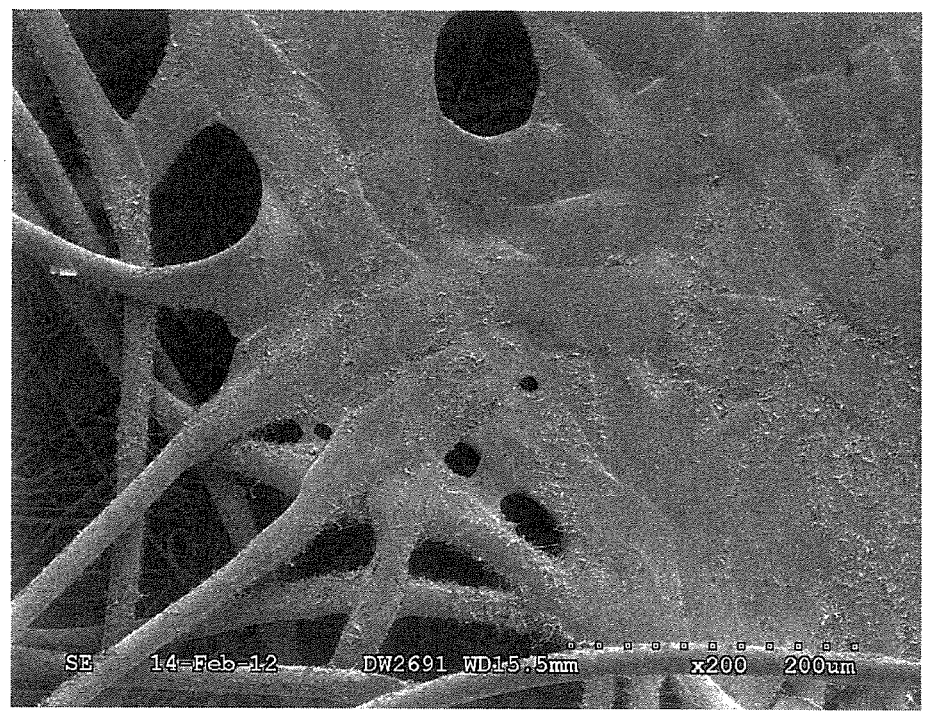
FIG. 19 is a SEM photograph of a portion of a bond site having a bond area, wherein a plurality of fibrils extend from the bond area in accordance with a non-limiting embodiment.

In an embodiment, a nonwoven substrate may have bond sites, like the bond sites 168, 268 described above in reference to FIGS. 5 and 7. The bond sites may each have a bond area. FIG. 19 illustrates an SEM photograph at 200 times magnification of fibrils that have grown from a portion of a bond site within the bond area after the bond site was created in a nonwoven substrate. This photograph was taken at least 100 hours after the bond site (e.g., a calendar bond) was formed in the nonwoven substrate. The nonwoven substrate of FIG. 19 is an SM nonwoven substrate, wherein the spunbond fibers of the nonwoven substrate were formed from a composition comprising 10% of the lipid ester glycerol tristearate by weight of the composition. The meltblown layer in FIG. 19 does not comprise fibers having fibrils, although the meltblown fibers (and fine fibers) having fibrils is within the scope of the present disclosure. The spunbond layer is 13 gsm, while the meltblown layer is 1 gsm. The fibrils may extend outwardly from a surface of the bond site. In such an embodiment, the layers of fibers of the nonwoven substrate were formed and then calender bonded or otherwise bonded (e.g., using the rolls 138 and 140 of FIG. 4), then the fibrils grew outwardly from the surface of the bond site from the fibers in one or more of the layers of the nonwoven substrate. Packages, packaging materials, and wipes of the present disclosure may also comprise nonwoven substrates comprising a layer of fibers comprising bond sites, wherein each bond site comprises a bond area, and wherein a plurality of fibrils extend outwardly from a surface of the bond area.

Figure 20:
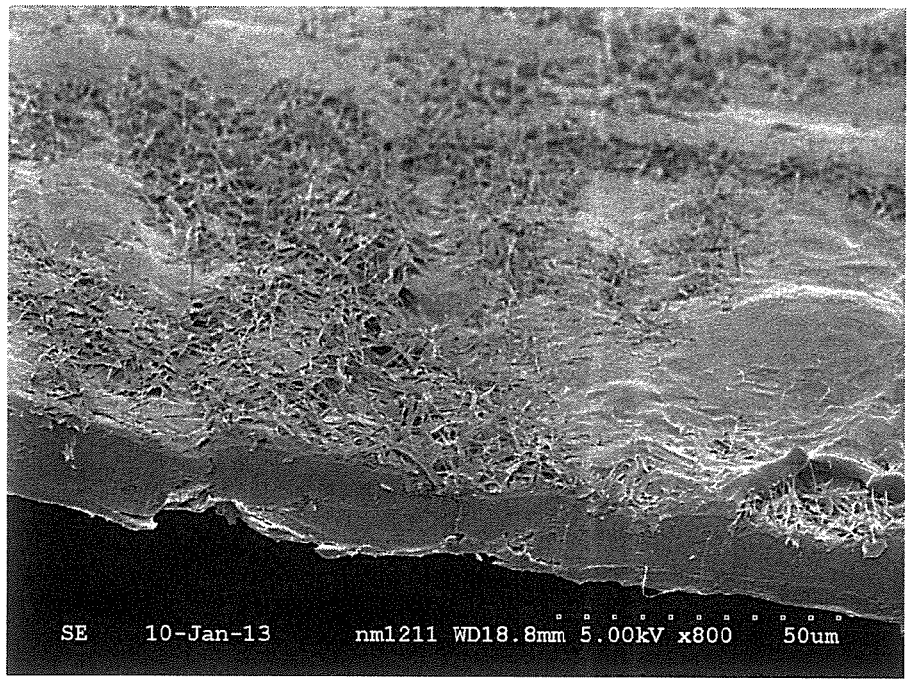
FIGS. 20-22 are SEM photographs of cross-sectional views of portions of a bond site having a bond area of a nonwoven substrate, wherein a plurality of fibrils extend from the bond area in accordance with various non-limiting embodiments.
Figure 21:
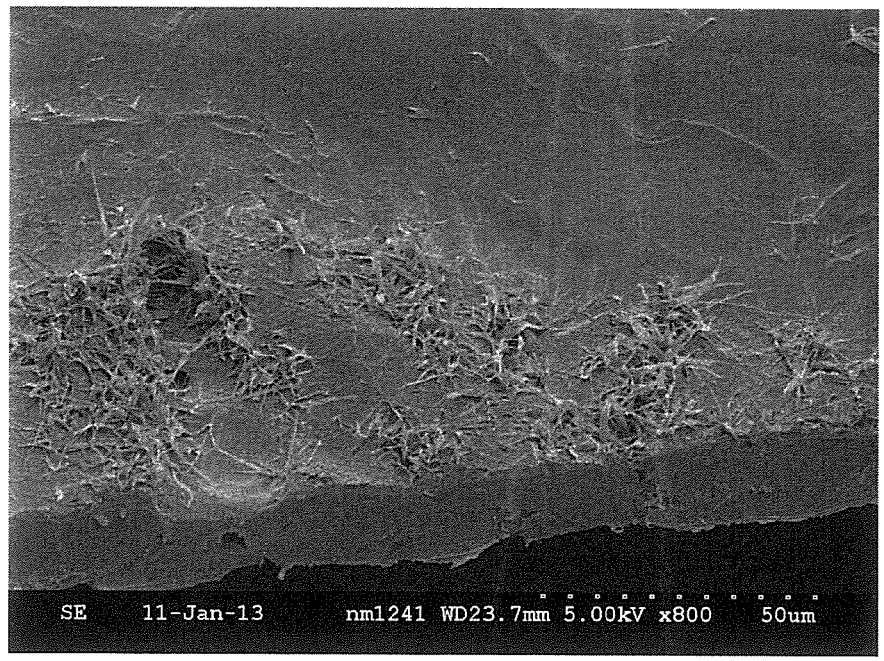
Figure 22:
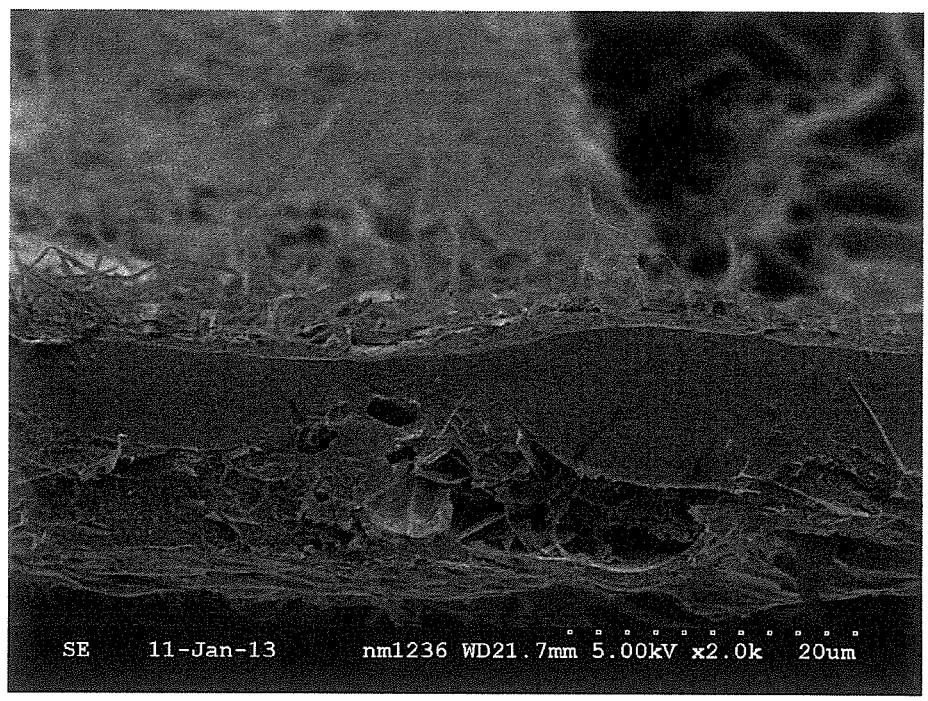

FIGS. 20-22 are SEM photographs of cross-sectional views taken about a portion of a bond site of an SMNS nonwoven substrate having a basis weight of 18 gsm. The spunbond fibers of the nonwoven substrate are formed from a composition comprising 10% of glycerol tristearate by weight of the composition. At least some of the spunbond fibers comprise fibrils. The meltblown layer and the fine fiber layer do not have fibers comprising fibrils in FIGS. 20-22, although the meltblown and fine fibers having fibrils is within the scope of the present disclosure.

In an embodiment, the composition used to create a layer of fibers, wherein at least some of, or all of, the fibers comprise fibrils extending outwardly therefrom, may comprise polyolefins and one or more melt additives, such as lipid ester melt additives, or any of the materials discussed herein with respect to fibers compositions with the melt additives. The polyolefins may comprise polypropylene, polyethylene, or other polyolefins, such as polybutylene or polyisobutylene, for example. The melt additives or lipid esters may be present in the composition, by weight of the composition, in the range of 2% to 45%, 11% to 35%, 11% to 30%, 11% to 25%, 11% to 20%, 11% to 18%, 11% to 15%, 11% to 15%, 3%, 5%, 10%, 11%, 12%, 15%, 20%, 25%, 30%, 35%, or 40%, specifically reciting all 0.5% increments within the above-specified ranges and all ranges formed therein or thereby. The melt additives suitable for the present disclosure may be hydrophobic melt additives. Thus, the melt additives may increase the hydrophobicity of the fibers in the layers of fibers, especially when the fibrils grow out of the fibers. This leads to increased low surface tension fluid strikethrough times and higher hydrophobicity for the layer of fibers within the nonwoven substrates and/or the nonwoven substrates themselves when compared to nonwoven substrates not having at least one layer formed from a composition comprising the one or more melt additives. This can also lead to better filtration and/or particular capturing properties when compared to conventional nonwoven substrates.

The melt additives of the present disclosure, namely the lipid esters, may have a melting point in the range of 30° C. to 160° C., 40° C. to 150° C., 50° C. to 140° C., 50° C. to 120° C., 50° C. to 100° C., 60° C. to 80° C., 60° C. to 70° C., about 60° C., about 65° C., or about 70° C., specifically reciting all one degree C. increments within the specified ranges and all ranges formed therein or thereby. In various embodiments, the melt additives of the present disclosure may have a melting temperature above 30° C., above 40° C., or above 50° C., but less than 200° C. or less than 150° C.

The melt additives used in the composition may comprise fatty acid derivatives, such as a fatty acid ester; typically an ester formed from an alcohol with two or more hydroxyl groups and one or more fatty acids having at least 8 carbon atoms, at least 12 carbon atoms, or at least 14 carbon atoms, whereby within one ester compound, different fatty acid-derived groups may be present (herein referred to as fatty acid ester).

The fatty acid ester compound may be an ester of an alcohol carrying two or more, or three or more, functional hydroxyl group per alcohol molecule, whereby all of the hydroxyl groups form an ester bond with fatty acids (either the fatty acid or mixtures thereof).

In an embodiment, the alcohol may have three functional hydroxyl groups.

In an embodiment, the one or more melt additives may comprise a mono- and/or di-glyceride ester, and/or a triglyceride ester, (with one, two or three fatty acid-derived groups).

The fatty acids used to form the ester compounds include fatty acid derivatives for the purpose of the present disclosure. A mono-fatty acid ester, or for example, amono-glyceride, comprises a single fatty acid, e.g., connected a glycerol; a di-fatty acid ester, or e.g., di-glyceride, comprises two fatty acids, e.g., connected to the glycerol; a tri-fatty acid ester, or e.g. tri-glyceride, comprises three fatty acids, e.g., connected to a glycerol. In an embodiment, the melt additive may comprise at least a triglyceride ester of fatty acids (i.e., the same or different fatty acids).

It should be understood that the triglyceride ester may have an esterified glycerol backbone having no nonhydrogen substituents on the glycerol backbone; however, the glycerol backbone may also comprise other substituents.

In an embodiment, the glycerol backbone of the glycerol ester may only comprise hydrogen. The glyceride esters may also comprise polymerized (e.g., tri) glyceride esters, such as a polymerized, saturated glyceride esters.

In a fatty acid ester having more than one ester bond, such as in di- or tri-glycerides, the fatty acid-derived group may be the same, or they may be two or even three different fatty acids-derived groups.

The melt additive may comprise a mixture of mono-, di-, and/or tri-fatty acid ester (e.g., mono- di- and/or triglyceride) esters with the same fatty-acid derived group per molecule, and/or with different fatty acid-derived groups.

The fatty acids may originate from vegetable, animal, and/or synthetic sources. Some fatty acids may range from a C8 fatty acid to a C30 fatty acid, or from a C12 fatty acid to a C22 fatty acid. Suitable vegetable fatty acids typically include unsaturated fatty acids such as oleic acid, palmitic acid, linoleic acid, and linolenic acid. The fatty acid may be arachidec, stearic, palmitic, myristic, myristoleic, oleic, limoleic, linolenic, and/or arachidonic acid.

In another embodiment, a substantially saturated fatty acid may be used, particularly when saturation arises as a result of hydrogenation of fatty acid precursor. In an embodiment, a C18 fatty acid, or octadecanoic acid, or more commonly called stearic acid may be used to form an ester bond of the fatty acid ester herein; stearic acid may be derived from animal fat and oils as well as some vegetable oils. The stearic acid may also be prepared by hydrogenation of vegetable oils, such as cottonseed oil. The fatty acid ester herein may comprise fatty acids of mixed hydrogenated vegetable oil, such as one having CAS registration number 68334-28-1.

At least one stearic acid, at least two, or three stearic acids are connected to a glycerol, to form a glycerol tristearate, for the melt additive herein. A melt additive herein may comprise at least glycerol tristearate.

In an embodiment, the melt additive may comprise a glycerol tristearate (CAS No. 555-43-1), also known by such names as tristearin or 1,2,3-Trioctadecanoylglycerol. (In the following, the name glycerol tristearate will be used, and in case of doubt the CAS No., shall be seen as the primary identifier).

In an embodiment, the fatty acid ester of the melt additive may have a number-averaged molecular weight ranging from 500 to 2000, from 650 to 1200, or from 750 to 1000, specifically reciting all whole integer increments within the above-specified ranges and any ranges formed therein or thereby.

The melt additive may comprise very little or no halogen atoms; for example, the melt additive may comprise less than 5 wt. % halogen atoms (by weight of the melt additive), or less than 1 wt. %, or less than 0.1 wt. % of the melt additive; the melt additive may be substantially halogen-free.

In an embodiment, the melt additive may be or may comprise a lipid ester or glycerol tristearate. In various embodiments, the fibrils may comprise, consist of, or consist essentially of (i.e., 51% to 100%, 51% to 99%, 60% to 99%, 70% to 95%, 75% to 95%, 80% to 95%, specifically including all 0.1% increments within the specified ranges and all ranges formed therein or thereby) of the melt additive.

The master batch added to the composition from which the fibers of the present disclosure are formed may be the master batch disclosed in U.S. Pat. No. 8,026,188 to Mor.

Once the composition of the melt additive and the polyolefin is used to form a layer of fibers, the layer of fibers may be incorporated into a nonwoven substrate, as disclosed as an example in FIG. 4. The nonwoven substrates having one or more layers of fibers having a plurality of the fibers have fibrils extending therefrom may comprise the melt additives in the range of 1% to 35% by weight of the nonwoven substrate, depending on the concentration of the melt additive in the composition used to form the fibers and depending on how many of the layers of fibers of the nonwoven substrate have fibers comprising the melt additive. Other possible ranges of melt additives, by weight of the nonwoven substrates, may be 2% to 35%, 5% to 25%, 11% to 35%, 11% to 25%, 11% to 20%, 11% to 18%, 11% to 15%, 11%, 12%, 13%, 15%, or 18%, specifically including all 0.5% increments within the ranges specified in this paragraph and all ranges formed therein or thereby.

In an embodiment, the fibrils may grow out of the fibers post-nonwoven substrate formation (i.e., after the process illustrated in FIG. 4) under ambient conditions. The fibrils may be noticeable using an SEM after about 6 hours post-nonwoven substrate formation under ambient conditions. Fibril growth may reach a plateau after about 50 hours, 75 hours, 100 hours, 200 hours, or 300 hours post-nonwoven substrate formation under ambient conditions. The time range of noticeable fibril growth post-nonwoven substrate formation may be in the range of 5 hours to 300 hours, 6 hours to 200 hours, 6 hours to 100 hours, 6 hours to 24 hours, 6 hours to 48 hours, or 6 hours to 72 hours, under ambient conditions, specifically reciting all 1 minute increments within the above specified ranges and all ranges formed therein or thereby. The time to allow full fibril growth post-nonwoven substrate formation may be 12 hours, 24 hours, 48 hours, 60 hours, 72 hours, 100 hours, or 200 hours, for example, under ambient conditions.

A method of forming an absorbent article having one or more of the nonwoven substrates of the present disclosure is also provided. The absorbent article, as described in the methods, may be a diaper, training pant, adult incontinence product, and/or a sanitary tissue product, for example.

In an embodiment, a method of forming an absorbent article may comprise providing one or more nonwoven substrates each comprising one or more layers of fibers, wherein a plurality of the fibers, or all of the fibers, in the one or more of the layers comprises a plurality of fibrils extending outwardly, or radially outwardly, from a body and/or surface of the fibers. The fibrils may at least extend outwardly from a longitudinal central third of the fibers. The fibrils may comprise, consist of, or consist essentially of, one or more melt additives, such as a lipid ester or glycerol tristearate. The method may further comprise incorporating the one or more nonwoven substrates into the absorbent article. In an embodiment, the incorporating comprises forming at least a portion of a filmless liquid impervious material or backsheet of an absorbent article. In other embodiments, the incorporating comprises forming at least a portion of a filmless liquid pervious material or topsheet of an absorbent article. In still another embodiment, the incorporating comprises forming a portion of a barrier leg cuff or gasketing cuff of an absorbent article or another portion of the absorbent article, such as the core cover or dusting layer, for example.

In an embodiment, a method of forming a component of, or a portion of, an absorbent article, a package, or an article of commerce may comprise forming fibers used to create a first layer of a nonwoven substrate, wherein the fibers in the first layer are formed from a composition comprising a thermoplastic polymer and a lipid ester, such as glycerol tristearate. The method may comprise forming fibers used to create a second layer of the nonwoven substrate. The fibers of the second layer may or may not be formed from a composition comprising a lipid ester, such as glycerol tristearate, but may at least comprise a thermoplastic polymer. In an embodiment, the first layer may comprise spunbond fibers or meltblown fibers and the second layer may comprise spunbond fibers, meltblown fibers, or fine fibers. The method may further comprise bonding the first and second layers together and growing fibrils from at least some of the fibers under ambient conditions after a predetermined time (e.g., 6 hours to 100 hours or 24 hours to 300 hours) to form the nonwoven substrate. The fibrils may grow at least out of the central ⅓ of the longitudinal length of the fibers. The growing fibrils step may occur before or after the bonding step. The bonding may be calendar bonding, mechanical bonding, thermal bonding, and/or other bonding types known to those of skill in the art. The method may comprise forming fibers used to create at least a third layer (i.e., fourth layer, fifth layer etc.) of the nonwoven substrate. The fibers of the third layer may or may not be formed from a composition comprising a lipid ester, such as glycerol tristearate, but may at least comprise a thermoplastic polymer. The bonding step may include bonding the first, second, and at least third layers together to form the nonwoven substrate. The third, fourth, fifth etc. layer may comprise spunbond fibers, meltblown fiber, and/or fine fibers.

In another embodiment, a method of forming a component of an absorbent article may comprise the steps of providing one or more nonwoven substrates each comprising one or more layers of fibers, allowing a plurality of fibrils to grow out of the at least some of, or all of, the fibers post-nonwoven substrate formation under ambient conditions, and incorporating the nonwoven substrate into one or more of the components of the absorbent article. The incorporating step may be performed before or after the allowing step. The components may be one or more of a barrier leg cuff, a gasketing cuff, a topsheet or liquid pervious material, a backsheet or liquid impervious material, wings, core covers, dusting layers, or other components. The components may be filmless or may be combined with a film. The time period of fibril growth, post-nonwoven substrate formation, or fiber formation, may be at least 12 hours, at least 24 hours, at least 50 hours, at least 75 hours, at least 100 hours, or at least 200 hours.

In other embodiment, the method of forming an absorbent article may comprise the steps of providing one or more nonwoven substrates comprising one or more layers of fibers, allowing the nonwoven substrate to increase in specific surface area by at least 10%, 15%, 20%, 25%, 100%, 200% or more, but less than 400%, 350% or 300%, from 10% to 350%, or from 20% to 200%, specifically reciting all 1% increments within the specified ranges and all ranges formed therein or thereby, post-nonwoven substrate formation under ambient conditions, allowing fibrils to grow out of one or more of the layers post-nonwoven substrate formation under ambient conditions, and incorporating the nonwoven substrate into a portion of the absorbent article. The incorporating step may be performed before or after either or both of the allowing steps. The fibers having the fibrils may be spunbond fibers, meltblown fibers, and/or fine fibers. The time of increase in specific surface area post-nonwoven substrate formation under ambient conditions may be at least 6 hours, at least 24 hours, at least 48 hours, at least 60, hours, at least 100 hours, at least 200 hours, but less than 300 hours, specifically reciting all 1 minute increments within the specified ranges.

In yet another embodiment, a method of forming the absorbent article may comprise the steps of providing one or more nonwoven substrates each comprising one or more layers of fibers, allowing the one or more nonwoven substrates to increase in specific surface area by at least 10%, 15%, 20%, 25%, 100%, 200%, or 300% post-fiber formation under ambient conditions of the one or more layer of fibers, and incorporating the nonwoven substrate into the absorbent article. The incorporating step may occur before or after the allowing step.

In an embodiment, the nonwoven substrates of the present disclosure may comprise one or more layers of fibers comprising fibrils. The nonwoven substrates, post-fibril growth under ambient conditions, may have specific surface areas in the range of 0.3 m$^2$/g to 7 m$^2$/g, 0.5 m$^2$/g to 5 m$^2$/g, 0.6 m$^2$/g to 3.5 m$^2$/g, 0.7 m$^2$/g to 3 m$^2$/g, 0.7 m$^2$/g to 1.5 m$^2$/g, 0.84 m$^2$/g to 3.5 m$^2$/g, or above 1.15 m$^2$/g, specifically including all 0.1 m$^2$/g increments within the above-specified ranges and all ranges formed therein or thereby.

Figure 23:
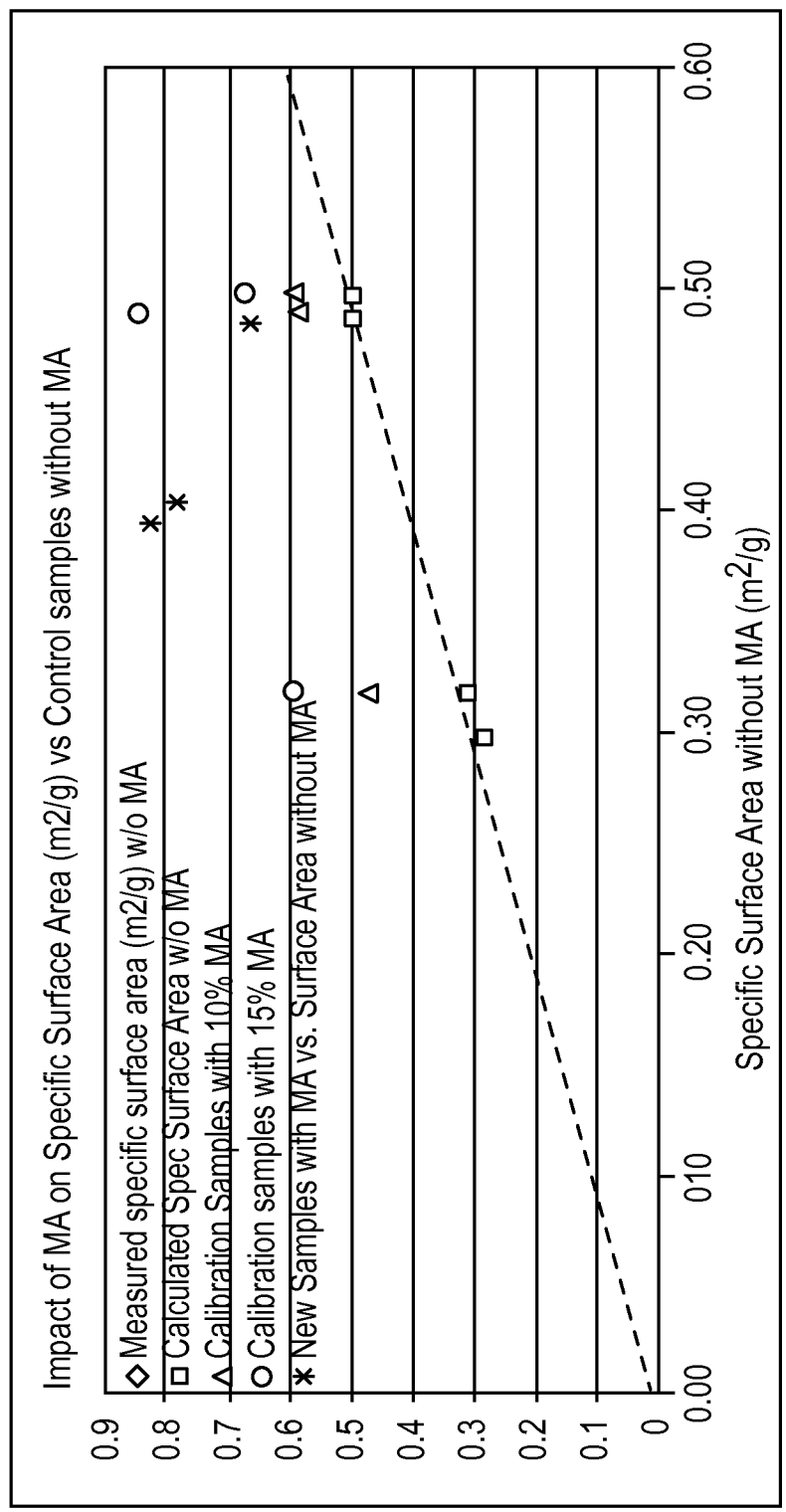
FIG. 23 is an example graph of the impact of the melt additive glycerol tristearate on specific surface area of nonwoven substrates of the present disclosure compared to the specific surface area of conventional nonwoven substrates without any glycerol tristearate in accordance with a non-limiting embodiment.

FIG. 23 illustrates a graph of specific surface areas of conventional nonwoven substrates (various SM and SMN samples without a lipid ester melt additive of the present disclosure) compared to specific surface areas of the same nonwoven substrates the lipid ester melt additive according to the present disclosure. The X axis in the figure represents the specific surface area without the fibrils and the Y axis in the figure represents the specific surface area with the fibrils. The nonwoven substrates of the present disclosure of FIG. 23 are formed from a composition comprising 10% (triangles in the figures) or 15% (circles in the figure) glycerol tristearate by weight of the composition in the spunbond layer of the samples, while the conventional nonwoven substrates (diamonds in the figure) do not have any glycerol tristearate in their fiber compositions. The dotted line represents the specific surface areas of the conventional nonwoven substrates. The calculated specific surface areas of the conventional nonwoven substrates without glycerol tristearate are illustrated as hollow rectangles in the figure. As will be seen, the specific surface areas of the nonwoven substrates of the present disclosure comprising fibers formed from a composition having 10% or 15% glycerol tristearate, by weight of the composition of the spunlaid fibers, are much higher than specific surface areas of conventional nonwoven substrates not having the glycerol tristearate in their fiber compositions. The asterisks in the figure represent samples of SMN nonwoven substrates with 1 gsm M and 1 gsm N each and a 13 gsm (lower values in the chart, about 0.67) or 19 gsm (higher values in the chart) spunbond layer having 10-15% glycerol tri-stearate, by weight of the composition used to form the spunbond fibers. These samples have not been produced without the melt additive of the present disclosure and are shown to be in the expected, predicted range of specific surface areas which are 20% to 100% higher than the samples would be without the melt additive.

In an embodiment, the nonwoven substrates of the present disclosure may have a low surface tension fluid strikethrough time (according to the LOW SURFACE TENSION FLUID STRIKETHROUGH TIME TEST below) to basis weight (according to the BASIS WEIGHT TEST below) ratio of 0.35 s/gsm to 5.0 s/gsm, 0.37 s/gsm to 5.0 s/gsm, 0.4 s/gsm to 4 s/gsm, 0.35 s/gsm to 15 s/gsm, 0.5 s/gsm to 15 s/gsm, is/gsm to 10 s/gsm, 2 s/gsm to 4 s/gsm, above 0.37 s/gsm, above 0.38 s/gsm, or above 0.4 s/gsm, specifically reciting all 0.1 s/gsm increments within the above specified ranges and all ranges formed therein or thereby. This ratio may be higher when more lipid ester melt additive is present in a nonwoven substrate and lower when less lipid ester melt additive is present in a nonwoven substrate.

Figure 24:
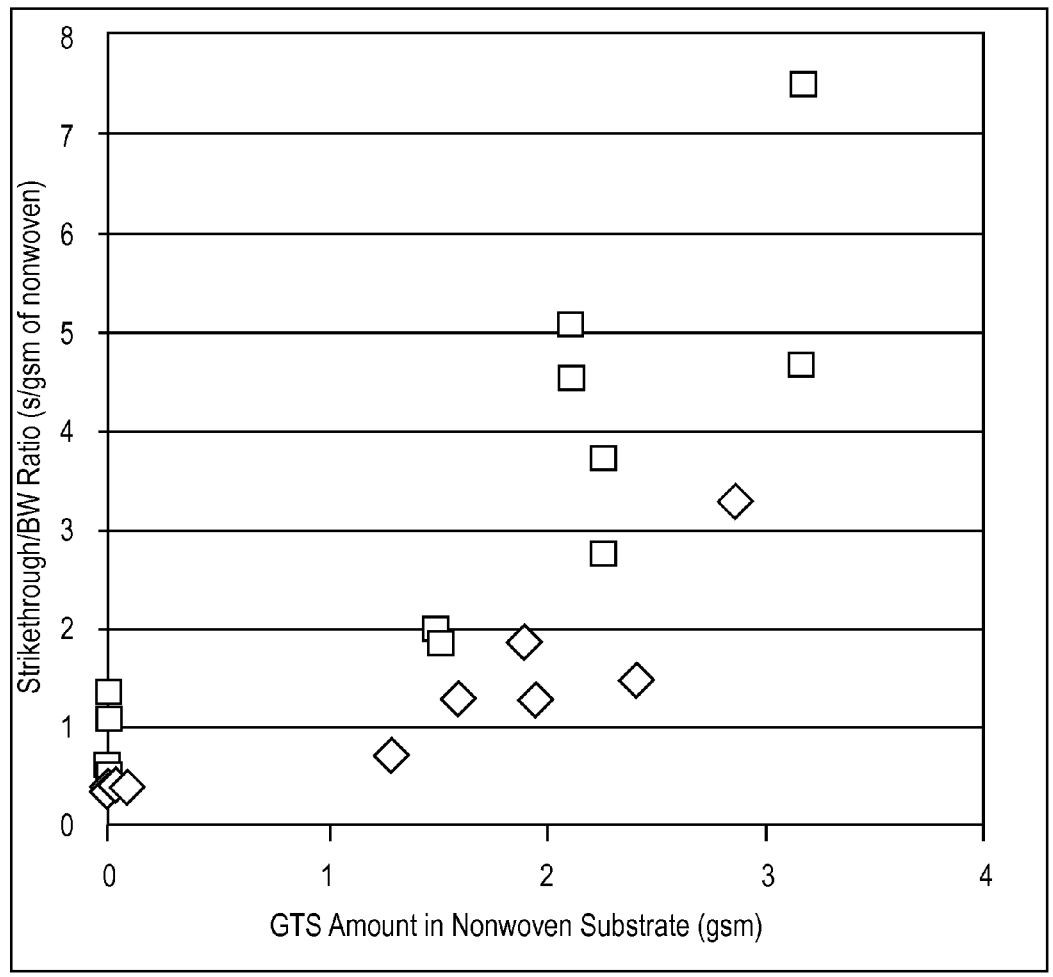
FIG. 24 is an example graph of low surface tension fluid strikethrough time (seconds) to basis weight (gsm) ratio (seconds/gsm) to the amount of glycerol tristearate (gsm) in a nonwoven substrate in accordance with a non-limiting embodiment.

FIG. 24 illustrates a graph of low surface tension fluid strikethrough time (seconds) to basis weight (gsm) ratio (seconds/gsm) compared to the basis weight (gsm) of glycerol tristearate within the nonwoven substrates. The diamonds represent SM or SMS nonwoven substrates and the rectangles represent SMNS and SMN nonwoven substrates. The samples indicated by diamonds have the same basis weight for both the SM and SMS nonwoven substrate samples. The samples indicated by rectangles have the same basis weight for both the SMNS and SMS nonwoven substrate samples. The X-axis in the figure represents the glycerol tristearate basis weight in the nonwoven substrates tested. The Y-axis in the figure represents the low surface tension fluid strikethrough time (seconds) to basis weight (gsm) ratio (seconds/gsm) of the nonwoven substrates tested. There is at least a 30% change in the strikethrough to basis weight ratio for about every 0.5 gsm of glycerol tristearate within the nonwoven substrates. In some instances, there is about a 100% change in the strikethrough to basis weight ratio for every 1 gsm of glycerol tristearate within the nonwoven substrates.

In an embodiment, an absorbent article may comprise a nonwoven substrate comprising one or more layers of fibers. The fibers may or may not comprise fibrils extending outwardly from a surface of the fibers. The nonwoven substrate may increase in specific surface area by at least 5%, at least 10%, at least 15%, at least 20%, at least 25%, at least 50%, at least 100%, at least 200%, at least 300%, or in the ranges of 10% to 300%, 10% to 250%, or 20% to 200%, specifically reciting all 0.5% increments within the specified ranges and any ranges formed therein or thereby, over a predetermined time period post-nonwoven substrate formation under ambient conditions. The predetermined time period may be greater than 6 hours and less than 200 hours or greater than 12 hours and less than 120 hours. The predetermined time period post-nonwoven substrate formation may also be the same as stated herein.

Figure 25:
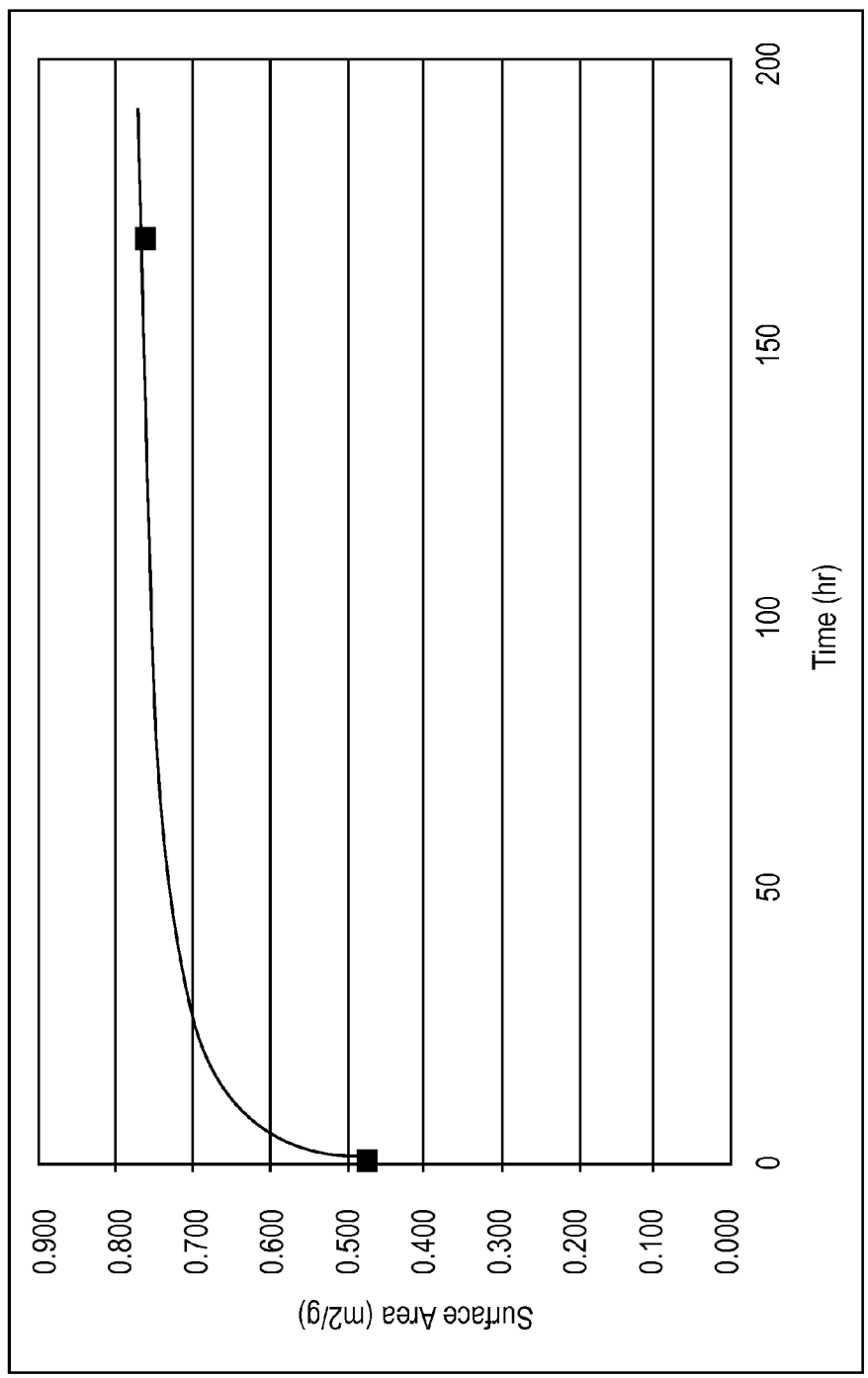
FIG. 25 is an example graph of specific surface area ($m^2/g$) to time (hours) post-nonwoven substrate or nonwoven layer formation for nonwoven substrates of the present disclosure in accordance with a non-limiting embodiment.

While not intending to be bound by any particular theory, FIG. 25 illustrates an example graph of the specific surface area (m$^2$/g) of a nonwoven substrate of the present disclosure having 15% glycerol tristearate, by weight of the composition used to produce the spunbond fibers, increasing over time. No glycerol tristearate is present in the meltblown or fine fibers in this example. The nonwoven substrate graphically illustrated in FIG. 25 is a 13 gsm SMN nonwoven substrate. The specific surface area increases post-fiber formation and/or post-nonwoven substrate formation under ambient conditions.

Figure 26:
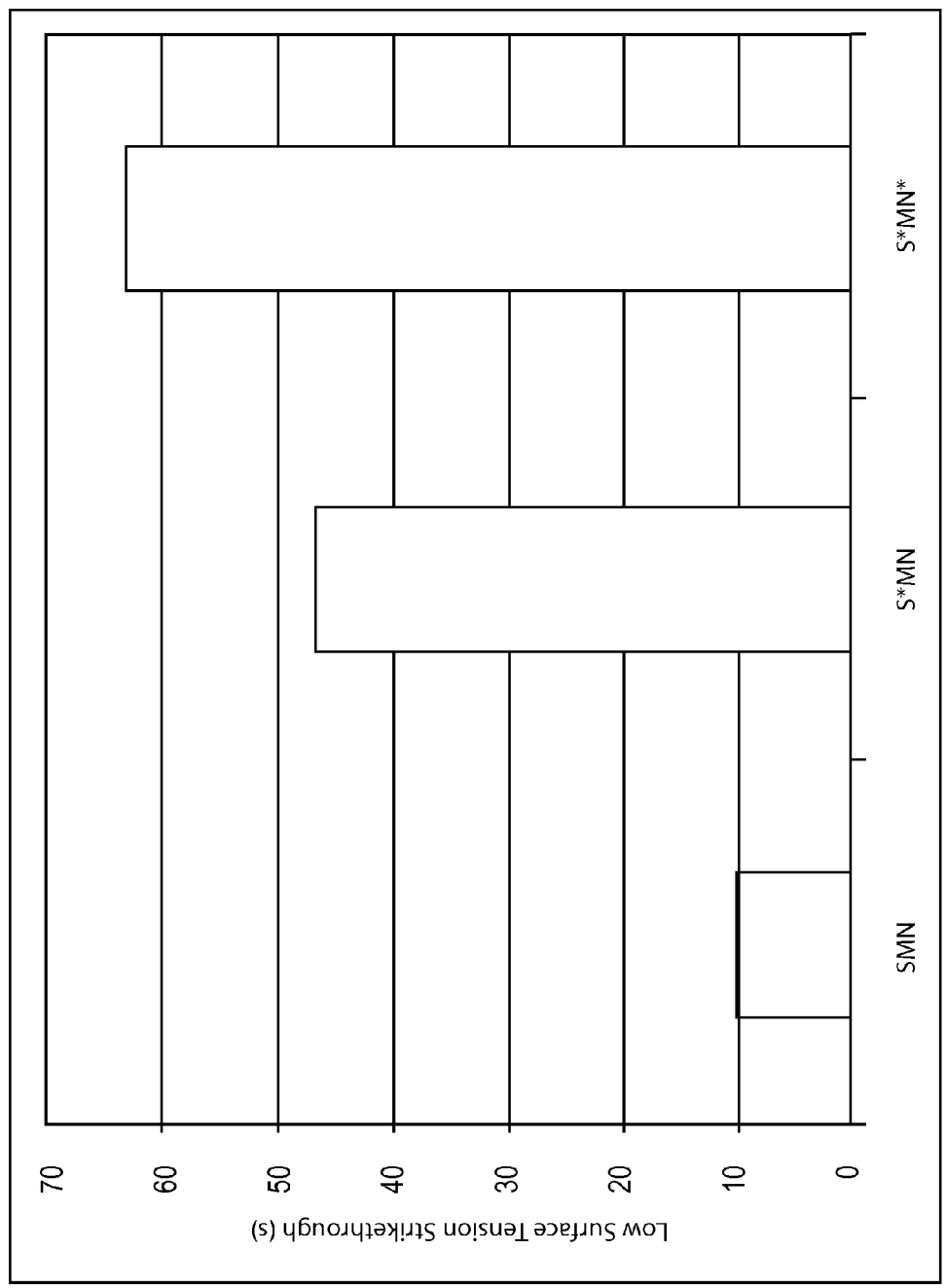
FIG. 26 is an example bar graph of low surface tension fluid strikethrough times (seconds) on various nonwoven substrates of the present disclosure compared to a conventional SMS 13 gsm nonwoven substrate in accordance with a non-limiting embodiment.

Referring to FIG. 26, low surface tension fluid liquid strikethrough times (seconds) are graphed for various nonwoven substrates of the present disclosure. All of the nonwoven substrates of the present disclosure are 13 gsm SMN nonwoven substrates. An asterisk refers to a layer with GTS in the layer. The asterisk after the S layer indicates that the spunbond fibers having fibrils were formed from a composition comprising about 10% GTS, by weight of the composition, while the asterisk after the N layer indicates that the nanofibers were formed from a composition comprising about 1% GTS, by weight of the composition. As can be seen from FIG. 26, the more layers comprising glycerol tristearate and thereby fibrils, the higher the low surface tension strikethrough time will be. The strikethrough times for a conventional 13 gsm SMN nonwoven substrate is also graphically illustrated in FIG. 26 for comparison.

Figure 27:
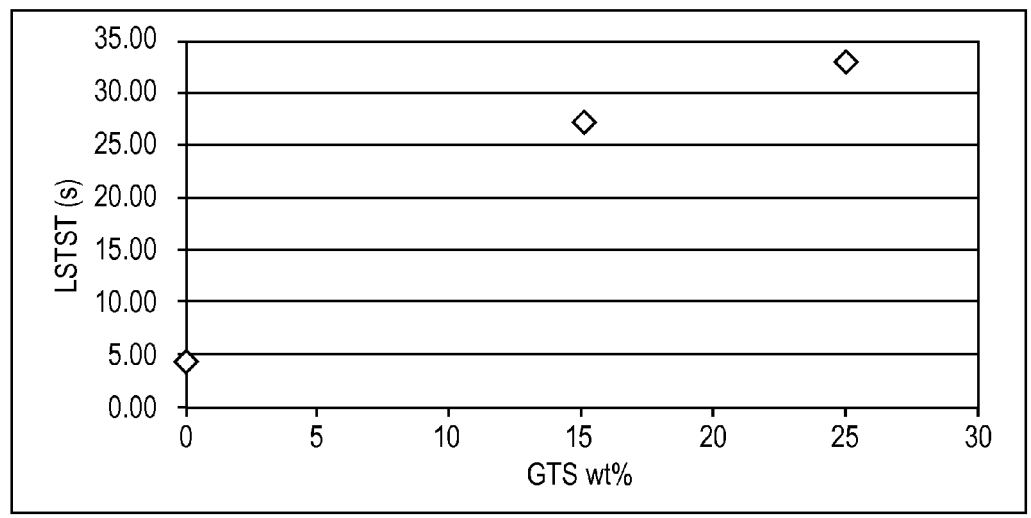
FIG. 27 is an example graph of low surface tension fluid strikethrough times (seconds) based on the glycerol tristearate percentages by weight of the composition used to form the fibers in accordance with a non-limiting embodiment.

Referring to FIG. 27, the low surface tension fluid strikethrough time in seconds (Y-axis) increases in the nonwoven substrates of the present disclosure as the glycerol tristearate percent, by weight of the composition used to form the fibers, increases. The samples of FIG. 27 are 50 gsm spunbond substrates having about 20 micrometer fibers.

Figure 28:
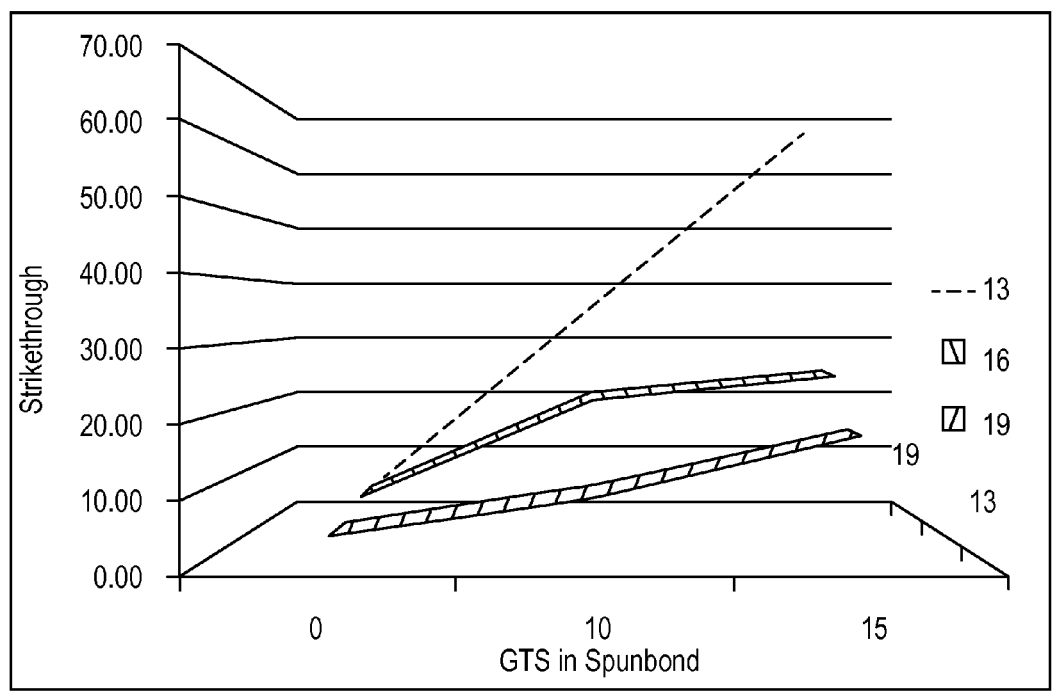
FIG. 28 is an example graph of low surface tension fluid strikethrough times (seconds) based on the percentages of glycerol tristearate by weight of the composition used to form the fibers in accordance with a non-limiting embodiment. The bottom line represents a 19 gsm spunbond nonwoven substrate. The middle line represents a 16 gsm spunbond nonwoven substrate. The top line represents a 13 gsm spunbond nonwoven substrate.

Referring to FIG. 28, the low surface tension fluid strikethrough time in seconds (Y-axis) increases in the nonwoven substrates of the present disclosure as the glycerol tristearate percent, by weight of the composition used to form the fibers (X-axis), and the basis weight of the nonwoven substrate increases. The samples of FIG. 28 illustrate a spunbond nonwoven substrate having a basis weight of 13 gsm (bottom line in the figure), a spunbond nonwoven substrate having a basis weight of 16 gsm (middle line in the figure), and a spunbond nonwoven substrate having a basis weight of 19 gsm (top line in the figure). As can be seen in the graph of FIG. 28, the strikethrough time goes up significantly as the % glycerol tristearate, by weight of the composition used to form the fibers increases, and as the basis weight of the nonwoven substrate increases.

Figure 29:
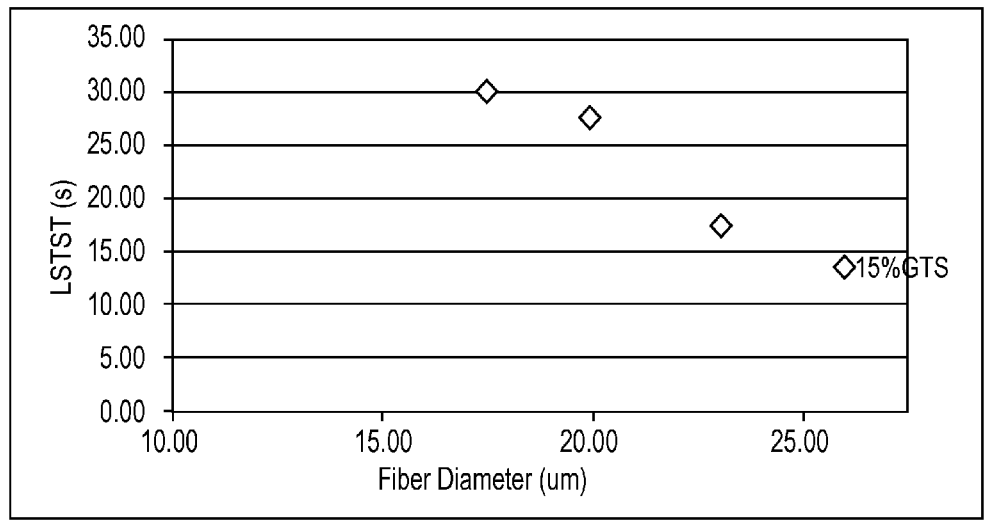
FIG. 29 is an example graph of low surface tension fluid strikethrough times (seconds) based on fiber diameters (μm) in accordance with a non-limiting embodiment.

Referring to FIG. 29, the low surface tension fluid strikethrough time in seconds (Y-axis) of the nonwoven substrates of the present disclosure decreases as the fiber diameter increases. All samples have 15% glycerol tristearate, by weight of the composition used to form the fibers. The samples of FIG. 29 are 50 gsm spunbond substrates.

Figure 30:
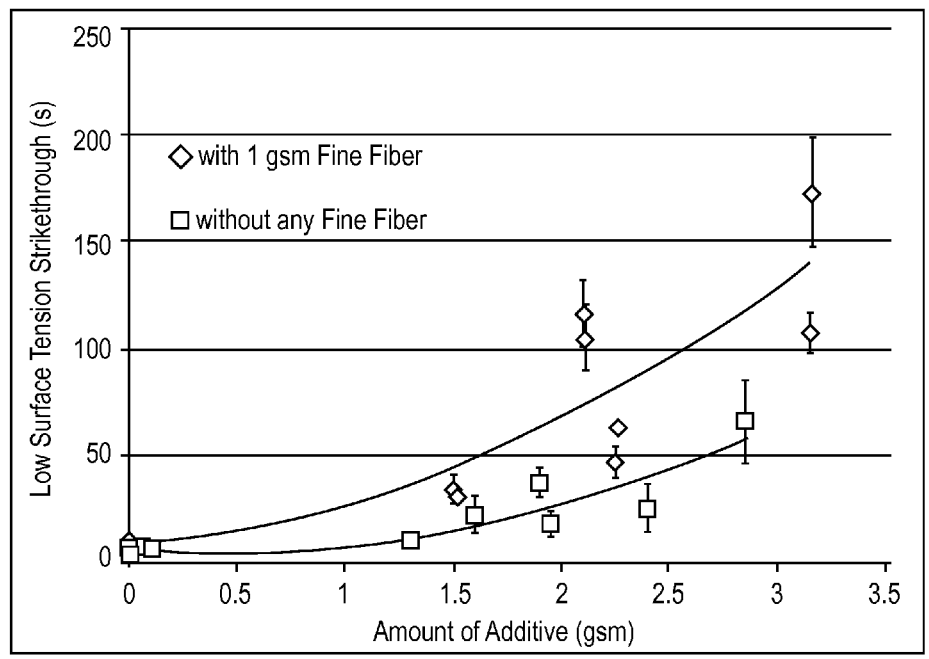
FIG. 30 is an example graph of low surface tension fluid strikethrough time (seconds) based on the amount of glycerol tristearate (gsm) within various nonwoven substrates in accordance with a non-limiting embodiment.

Referring to FIG. 30, the low surface tension fluid strikethrough time in seconds (Y-axis) of the nonwoven substrates of the present disclosure increases as more fine fibers are added to the nonwoven substrates and/or as the basis weight of the glycerol tristearate within the nonwoven substrate increases (X-axis). The top line in the graph is from a nonwoven substrate (SMN) having spunbond/meltblown fibers formed from a composition having 10% glycerol tristearate, by weight of the composition, and 1 gsm of fine fibers not having any glycerol tristearate. The bottom line in the graph is from a nonwoven substrate having spunbond/meltblown fibers formed from a composition having 10% glycerol tristearate, by weight of the composition, and no fine fibers (SM). The top line has 1 gsm extra of basis weight compared to the bottom line owing to the addition of the 1 gsm of fine fibers.

In an embodiment, the nonwoven substrates of the present disclosure may comprise one or more layers each comprising a plurality of fibers, wherein at least some of the fibers, or all of the fibers, comprise fibrils extending outwardly or radially outwardly from a surface thereof. The nonwoven substrates may be used as a receiving component in an absorbent article fastening system. The receiving component may be configured to receiving a fastening tab of the fastening system 70 or another fastening tab or member. In an embodiment, the nonwoven substrate may form all of, or a portion of, a nonwoven landing zone for one or more fastening tabs or members. The fastening tabs or members may have hooks (e.g., a side of a hook and loop fastener) that engages the nonwoven substrate. Owing to the specific surface area increase in the nonwoven substrates post-nonwoven substrate formation compared to conventional nonwoven substrates and because of the fibrils, the nonwoven substrates of the present disclosure may provide better attachment of the hooks to the nonwoven substrates. Example suitable nonwoven landing zone bonding patterns and other considerations for the nonwoven substrates of the present disclosure may be found in U.S. Pat. No. 7,895,718 to Horn et al., U.S. Pat. No. 7,789,870 to Horn et al. and U.S. patent application Ser. No. 13/538,140 to Ashraf et al., Ser. No. 13/538,177 to Ashraf et al., and Ser. No. 13/538,178 to Rane et al.

When used as a fluid permeable layer (e.g., topsheet), the nonwoven substrates of the present disclosure may tend to retain fluid, running BM, or menses less than conventional nonwoven substrates and thus may drain more completely to the underlying absorbent core, thereby leaving a more clean-looking and clean-feeling topsheet. Example nonwoven substrates that may be used as fluid permeable layers may be unapertured low density structures, such as a spunlaid structures with relatively high caliper and porosity, or apertured nonwoven substrates.

The nonwoven substrates of the present disclosure having at least one layer comprising fibers comprising fibrils may be configured to be softer or harder than, or have the same softness as, conventional nonwoven substrates and/or may have a rougher, smoother, or the same tactile property as compared to conventional nonwoven substrates. The softness, hardness, and/or tactile property of the nonwoven substrates may vary depending on the type and amount of lipid esters present in the composition used to form the fibers and the length of the fibrils, for example. The softness, hardness, and/or texture may also vary depending on where the one or more layers of fibers having fibrils are positioned within a nonwoven substrate.

In an embodiment, one or more of the nonwoven substrates of the present disclosure may be used as a filtration media, a filter, or portion thereof, for various fluids (i.e., liquids (e.g., water) or gases (e.g., air)). The fibrils, and thereby the increased surface area of the fibers, may allow for better and/or more efficient filtration of the fluids by filtering out more particulate or undesirable materials in the fluids. This may increase the effective lifetime of the filter and/or filtration media as well. The concentration of the lipid esters by weight of the composition used to make the fibers may be increased to further promote more efficient filtration and/or lifetime of the filter and/or filtration media.

In an embodiment, the fibrils may have a different color than the fibers from which they grow. Stated another way, the fibrils may have a first color and the fibers from which they grow may have a second color in non-fibril areas of the fibers. The first color may be different than the second color (e.g., the fibers in non-fibril areas may be white and the fibrils may be blue or the fibers in non-fibril areas may be light blue and the fibrils may be dark blue). This color variation can be accomplished by adding a colorant, such as a pigment or dye to the lipid esters before they are mixed into the composition used to form the fibers. When the lipid esters grow from the fibers, they will be a different color than the fibers from which they grow, thereby producing a color contrast between the fibrils and the fibers from which they grow. In an embodiment, the layer of nonwoven substrate comprising the fibers comprising the fibrils may appear to change color over a period of time (i.e., the period of time in which the fibrils grow or a portion thereof) due to the contrasting color of the fibrils with respect to the fibers from which they grow. Different layers of fibers may have different colored fibrils and/or fiber therein within the same nonwoven substrate. In an embodiment, the colorant added to the lipid esters may be dissolvable in urine, menses, runny BM, other bodily fluid, or other fluid (e.g., water). In various embodiments, the dissolving colorant in the fibrils may be used as a wetness indicator in an absorbent article, for example. The fibers having colors different than their fibrils may be used in wipes or any portion of an article of commerce, such as an absorbent article.

Figure 31:
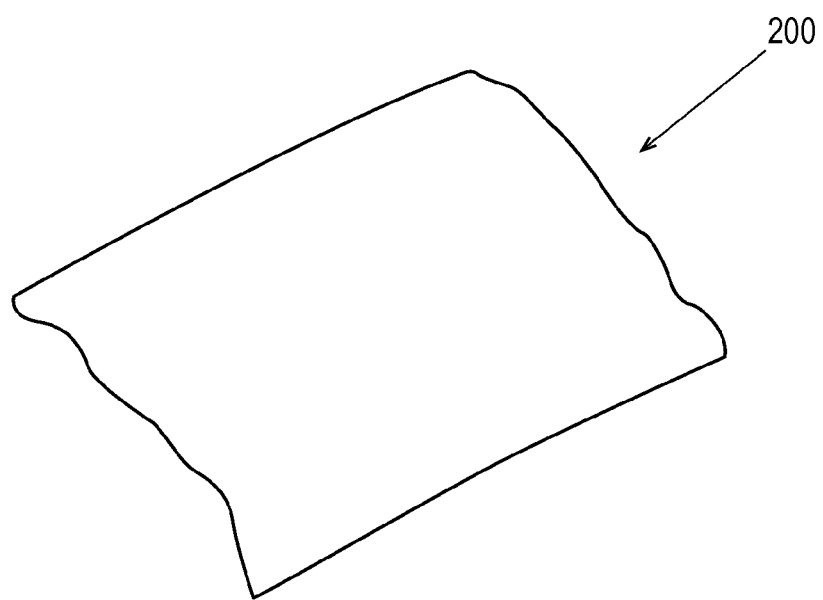
FIG. 31 is a perspective view of a wipe or cleaning substrate, wherein the wipe or cleaning substrate may comprise the nonwoven substrates of the present disclosure in accordance with a non-limiting embodiment.

The nonwoven substrates of the present disclosure may be used to form at least a portion of, or all of, any suitable article of commerce. Example articles of commerce are wet wipes, baby wet wipes, dry wipes, facial wipes, make-up removal/application wipes, medical wipes, bandages, and wraps, scrubbing wipes, shop towels, towels, cleaning wipes, sanitary wipes, cleaning substrates such as Swiffer®, and any other wipes and substrates (herein together referred to as "wipes"). An example wipe 200 is illustrated in FIG. 31. The wipes may benefit from the fibrils within at least one layer of fibers of the nonwoven substrates because of the better absorbency, scrubbing ability, particulate capture, particulate retention, dirt attraction, dirt retention, and/or application ability, for example, as a result of the fibrils. The fibrils may be formed of lipid esters or other melt additives which may have a wax-like feel or texture that can be helpful in attracting and retaining dirt particles and other matter.

The wipes, or the one or more nonwoven substrates having fibrils of the wipes, may comprise a composition. The composition may be applied to the fibers of the nonwoven substrate and/or may be at least partially comprised in or applied to the fibrils. The composition may comprise water, a fragrance, a soap, a makeup, a skin care composition, a lotion, a polish, a cleaning composition, other suitable compositions, and/or combinations thereof. The compositions may be in liquid, semi-liquid, paste, or solid form on the fibrils and/or when applied to the fibrils. In the event that the composition comprises moisture, such as water, the wipe may have 100% to 600%, 150% to 550%, or 200% to 500% weight of moisture relative to the dry weight of the wipe or relative to the dry weight of the nonwoven substrate within the wipe, specifically reciting all 1% increments within the above-specified ranges and any ranges formed therein or thereby. The wipe or the nonwoven substrate may have at least 10%, 20%, 30%, 40%, 50%, 75%, 100%, 150%, 200%, 300% or more of weight of the composition relative to the total weight of the wipe or relative to the total weight of the nonwoven substrate. Without intending to be bound by any theory, it is believed that nonwoven substrates having one or more layers of fibers comprising fibrils have a better affinity to compositions and/or a better ability to retain compositions to the nonwoven substrate. Therefore, it is believed that the fibrils and the nonwoven layer comprising the fibrils may absorb and stably retain higher amounts of compositions as compared to conventional nonwoven substrates not having fibrils. Furthermore, the fibrils may inhibit stratification in a stack of multiple wipes during storage and before use (i.e., inhibiting dryer wipes on the top of the stack and wetter wipes on the bottom of the stack) better than conventional nonwoven substrates without fibrils.

In an embodiment, at least some of the fibrils comprising the composition may be removable or separatable from the fibers when the wipe is rubbed against a surface, such as a surface to be cleaned or a bodily surface. The fibrils may separate from the fibers thereby applying the composition to the surface. Such separation may occur owing to frictional forces applied to the wipe when moved over the surface. In an example embodiment, the fibrils comprising the composition may be formed in a skin lotion applying wipe. When a user moves the wipe over a bodily surface, the fibrils may separate from the fibers to apply the skin lotion to the bodily surface. Other examples are also within the present disclosure.

In an embodiment, the nonwoven substrates of the present disclosure comprising one or more layers comprising fibers comprising fibrils may increase the acoustic dampening properties of the nonwoven substrates, compared to conventional nonwoven substrates, because of the fibrils causing an increase in the scattering of sounds waves as they pass through the nonwoven substrate. Further, the nonwoven substrates of the present disclosure may have better masking or opacity properties than conventional nonwoven substrates because of the scattering of light waves caused by the fibrils as light waves pass through the nonwoven substrates.

Figure 32:
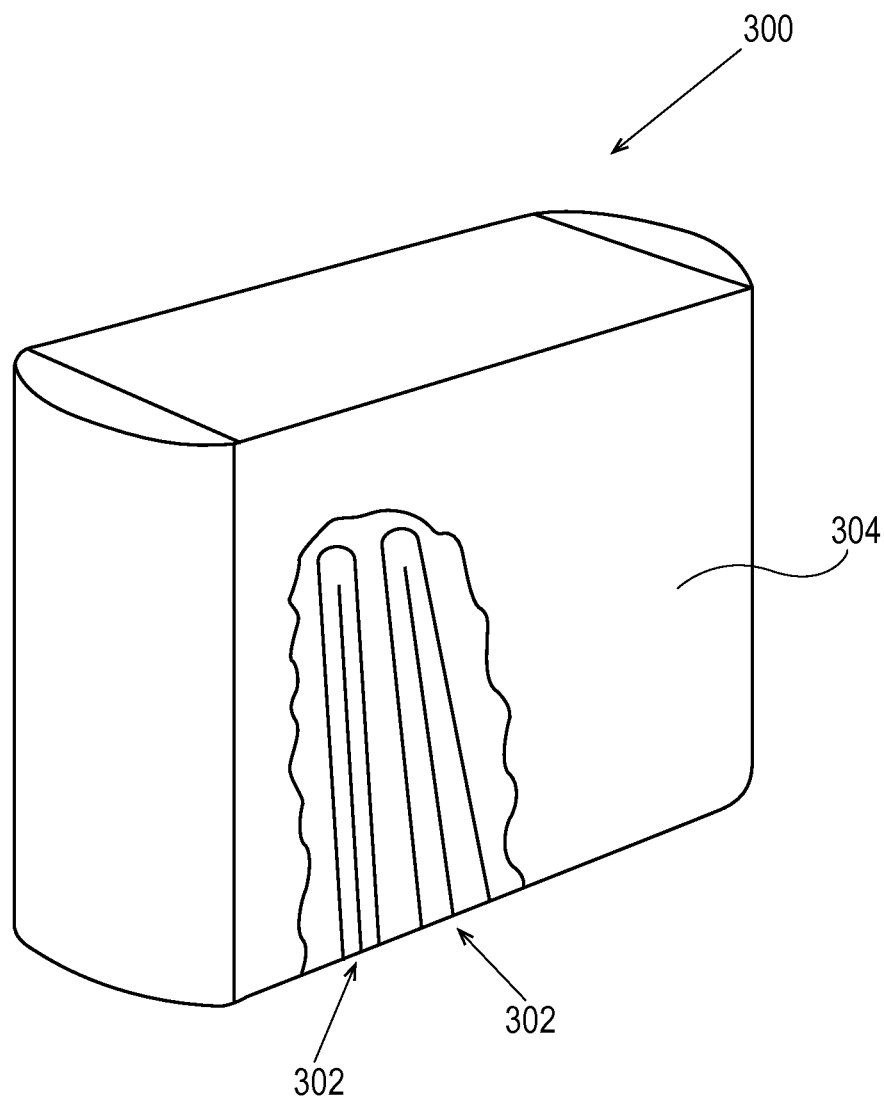
FIG. 32 is a perspective view of a package for articles of commerce, wherein a portion of the package may comprise the nonwoven substrates of the present disclosure in accordance with a non-limiting embodiment.

The nonwoven substrates of the present disclosure may be used as packaging materials or may be used to form at least portions of, or all of, packages. The packages may take on any suitable configuration, such as the configuration of one or more articles of commerce within the packages or any other configuration. Packaging materials, as used herein, also encompasses release liners that cover adhesives on sanitary napkins or absorbent articles or any other component placed on, attached to, or formed with a consumer product prior to sale or use even if that component does not form an outer portion of a package. In an embodiment, the nonwoven substrates may be used to form at least an outer portion, inner portion, or other portion of the packages. Referring to FIG. 32, the packages 300 may comprise one or more articles of commerce 302 and may be at least partially formed by the nonwoven substrates 304 of the present disclosure. The articles of commerce 302 may also have packaging materials formed from the nonwoven substrates of the present disclosure. A portion of the package 300 is cut away in FIG. 32 to illustrate example articles of commerce 302 within the package 300. The hydrophobic nature and high low surface tension fluid strikethrough times of the nonwoven substrates of the present disclosure provides them with good resistance to moisture infiltration into the packages, thereby maintaining the articles of commerce in a dry, or substantially dry state, while also providing some breathability to the packages. The nonwoven substrates may also be combined with other materials, such as films, to form packages or packaging materials. One typical packaging material for articles of commerce is films. The nonwoven substrates of the present disclosure may be free of film or use less film, thereby saving costs. The nonwoven substrates may also provide softer packaging materials than films.

In an embodiment, the lipid esters in the fibers having fibrils of the nonwoven substrates of the present disclosure may be free of droplets of lipid esters. "Free of droplets of lipid esters" means that the lipid ester (e.g., GTS) is substantially homogeneously, or homogeneously, distributed throughout the composition used to form the fibers in very fine particles (i.e., less than 300 nm, less than 200 nm, or less than 100 nm) and, thereby, throughout the fibers formed from the composition, and does not form pockets of lipid esters in the fibers. In cross-sections of fibers comprising lipid esters of the present disclosure, droplets cannot be seen at 8000 times magnification using an SEM (see e.g., FIG. 34 at 8,000 times magnification). Droplets, as used herein, have a minimum dimension of at least 300 nm and can be seen in SEMS cross-sections of a fiber at 8,000 times magnification, if present. Further, the fibers, once the lipid ester is dissolved using the Gravimetric Weight Loss Test set forth below, do not have void volumes left therein. Void volumes, as used herein, have a minimum dimension of 300 nm and can be seen at 8,000 times magnification of a fiber using a SEM. The fibers of the present disclosure do not have such droplets and, therefore, void volumes are not formed in the fibers post Gravimetric Weight Loss Test performance.

Figure 33:
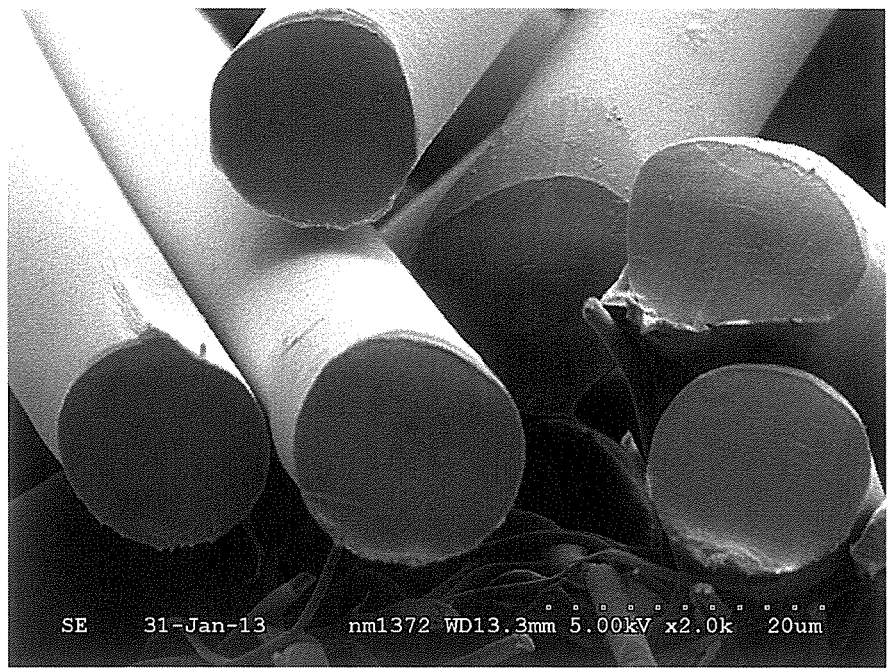
FIG. 33 is an SEM photograph of a cross-sectional view of a nonwoven substrate of the present disclosure, wherein the lipid esters in the spunbond fibers have been dissolved using a gravimetric weight loss method in accordance with a non-limiting embodiment.
Figure 34:
FIG. 34 is an SEM photograph of a cross-sectional view of a spunbond fiber of FIG. 33 in accordance with a non-limiting embodiment.

FIGS. 33 and 34 show cross-sectional views of fibers post-Gravimetric Weight Loss Test performance (e.g., after the lipid esters, such as GTS, in the fibers have been dissolved). The fibers in FIGS. 33 and 34 are of an 18 gsm SMNS material with about 10% glycerol tristearate, by weight of the composition used to form the S layers, wherein the M layer plus the N layer has a 2 gsm basis weight, after the GTS has been dissolved. As illustrated, no void volumes are present in the fibers owing to the substantially homogeneous, or homogeneous, distribution of the lipid esters within the fibers. Void volumes would have been created in the fibers if the fibers had droplets of lipid esters present therein. Since the fibers of the present disclosure are droplet-free, no void volumes are present in the fibers post-Gravimetric Weight Lost Test performance.

Components of the absorbent articles, packages, and articles of commerce described herein can at least partially be comprised of bio-sourced content as described in U.S. Pat. Appl. Publ. No. 2007/0219521A1 to Hird et al. published on Sep. 20, 2007, U.S. Pat. Appl. Publ. No. 2011/0139658A1 to Hird et al. published on Jun. 16, 2011, U.S. Pat. Appl. Publ. No. 2011/0139657A1 to Hird et al published on Jun. 16, 2011, U.S. Pat. Appl. Publ. No. 2011/0152812A1 to Hird et al. published on Jun. 23, 2011, U.S. Pat. Appl. Publ. No. 2011/0139662A1 to Hird et al. published on Jun. 16, 2011, and U.S. Pat. Appl. Publ. No. 2011/0139659A1 to Hird et al. published on Jun. 16, 2011. These components include, but are not limited to, topsheet nonwovens, backsheet films, backsheet nonwovens, side panel nonwovens, barrier leg cuff nonwovens, super absorbents, nonwoven acquisition layers, core wrap nonwovens, adhesives, fastener hooks, and fastener landing zone nonwovens and film bases.

In an embodiment, a disposable absorbent article component, an article of commerce component, or a package component may comprise a bio-based content value from about 10% to about 100% using ASTM D6866-10, method B, in another embodiment, from about 25% to about 75%, and in another embodiment, from about 50% to about 60% using ASTM D6866-10, method B.

In order to apply the methodology of ASTM D6866-10 to determine the bio-based content of any absorbent article component, package component, or article of commerce component, a representative sample of the absorbent article component, the package component, or the article of commerce component must be obtained for testing. In an embodiment, the absorbent article component, the package component, or the article of commerce component may be ground into particulates less than about 20 mesh using known grinding methods (e.g., Wiley® mill), and a representative sample of suitable mass taken from the randomly mixed particles.

Figure 35:
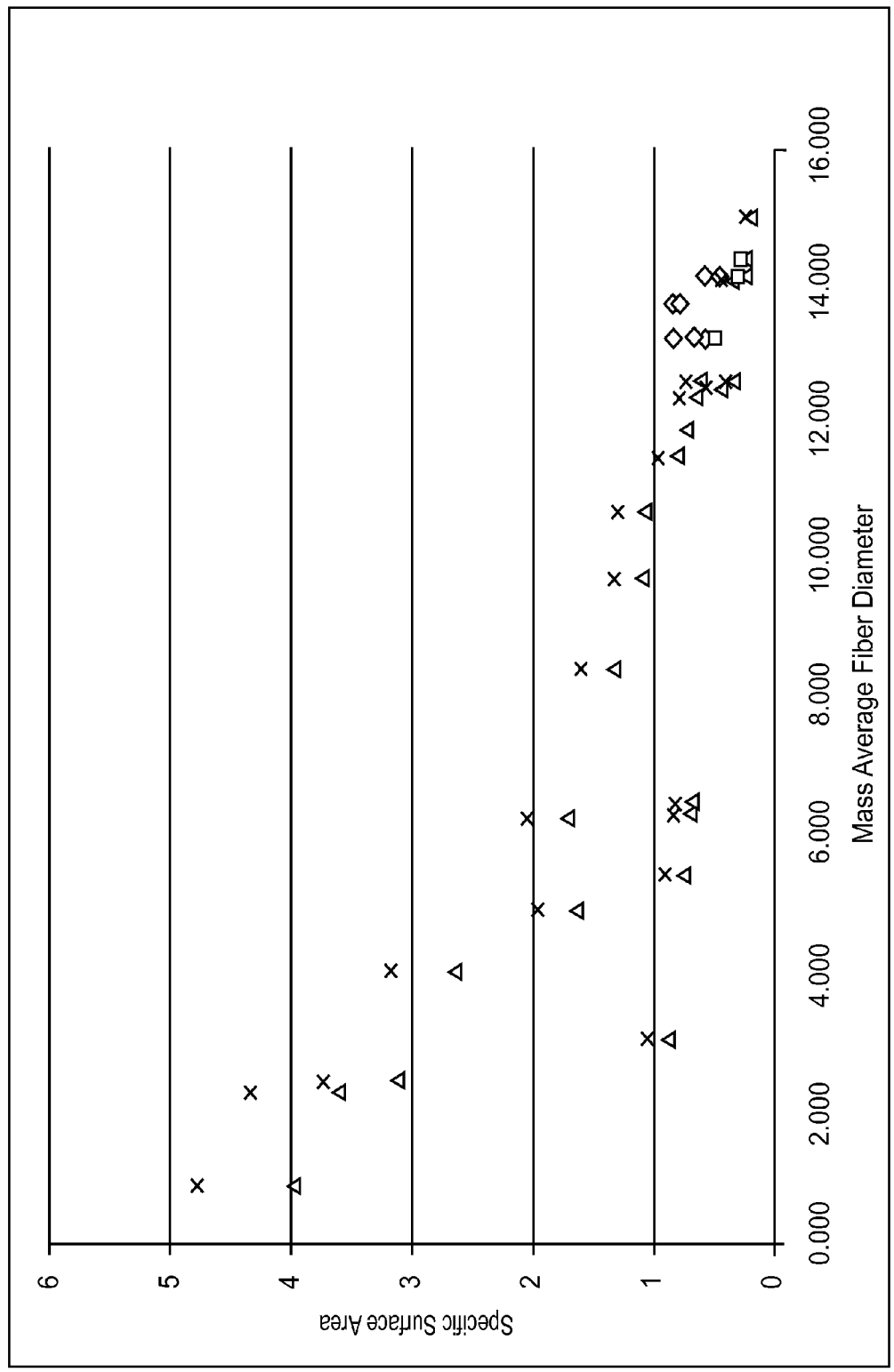
FIG. 35 is an example graph of mass-average fiber diameter (X-axis) to specific surface area (Y-axis) in accordance with a non-limiting embodiment.

FIG. 35 illustrates an example graph of mass-average fiber diameter (X-axis) vs. specific surface area (Y-axis). The triangles represent the calculated theoretical specific surface area of various S, SM, SMS, SMNS, and M nonwoven substrate samples without the presence of GTS in fibers thereof. The "Xs" represent the calculated theoretical specific surface area of the nonwoven substrate samples at the triangles plus a calculated 20% increase in the specific surface area. This 20% increase in the specific surface area represents the spunbond fibers being formed from a composition comprising about 10% to about 15% GTS by weight of the composition. If the fibers have a mass-average fiber diameter of less than 5, the about 10% to about 15% GTS would be added to the meltblown layer since those samples would not have a spunbond layer. The diamonds represent samples of various SMN nonwoven substrates having fibers, wherein some of the fibers were formed from compositions comprising GTS. The S layers were formed from a composition comprising about 10% to about 15% GTS, by weight of the composition, and one of the M or N layers were formed from a composition comprising 1% GTS by weight of the composition. The squares represent various samples of SMN nonwoven substrates without any GTS in any of the fibers thereof. Mass-average fiber diameter is set forth in μm and specific surface area is set forth in $m^2/g$. For a mass-average fiber diameter of above 8 μm, the specific surface area may be about 1.6 $m^2/g$ or more. For a mass-average fiber diameter of above 10 μm, the specific surface area may be about 1.2 $m^2/g$ or more. For a mass-average fiber diameter of above 12 μm, the specific surface area may be about 0.8 $m^2/g$ or more. In various embodiments, the specific surface area of the fibers of the present disclosure may be in the range of about 0.5 $m^2/g$ to about 10.0 $m^2/g$, about 0.7 $m^2/g$ to about 8.0 $m^2/g$, or even about 0.8 $m^2/g$ to about 6.0 $m^2/g$, specifically reciting all 0.1 $m^2/g$ increments within the specified ranges and all ranges formed therein or thereby.

In an embodiment, an absorbent article, a packaging material, and/or a wipe may comprise a one or more nonwoven substrates, each comprising a plurality of fibers, wherein at least some of the fibers may have a mass-average fiber diameter above 8 μm and a specific surface area of at least 1.6 $m^2/g$. In an embodiment, an absorbent article, a packaging material, and/or a wipe may comprise a one or more nonwoven substrates, each comprising a plurality of fibers, wherein at least some of the fibers may have a mass-average fiber diameter above 10 μm and a specific surface area of at least 1.2 $m^2/g$. In an embodiment, an absorbent article, a packaging material, and/or a wipe may comprise one or more nonwoven substrates, each comprising a plurality of fibers, wherein at least some of the fibers may have a mass-average fiber diameter above 12 μm and a specific surface area of at least 0.8 $m^2/g$. The absorbent articles may comprise a liquid pervious material, a liquid impervious material, and an absorbent core disposed at least partially intermediate the liquid pervious material and the liquid impervious material.

In an embodiment, an absorbent article may comprise a liquid pervious material, a liquid impervious material, and an absorbent core disposed at least partially intermediate the liquid pervious material and the liquid impervious material. The absorbent article may further comprise a nonwoven substrate comprising one or more layers of fibers. A plurality of the fibers may each comprise a plurality of fibrils extending outwardly from a surface of the fibers. The plurality of fibrils may comprise a lipid ester. A portion of, or all of, the liquid impervious material may comprise the nonwoven substrate and the liquid impervious material may be free of a film. A portion of, or all of, the liquid pervious material may comprise the nonwoven substrate and may be free of a film. The absorbent article may comprise a one or more barrier leg cuffs. A portion, or all of, the one or more barrier leg cuffs may comprise the nonwoven substrate and the barrier leg cuffs, or portions thereof, may be free of a film. The plurality of fibrils may comprise glycerol tristearate. The glycerol tristearate may have a melting temperature above 35° C. or may be in the range of 40° C. to 150° C. The plurality of fibers may be formed from a composition comprising a polyolefin and the lipid ester. The composition may comprise at least 11% of the lipid ester, by weight of the composition. The average length of the fibrils from the surfaces of the fibers to free ends of the fibrils may be in the range of 0.5 μm to 20 μm. The average hydraulic diameter of the fibrils may be in the range of 100 nm to 800 nm. The layer of fibers may comprise spunbond fibers, meltblown fibers, and/or fine fibers. At least some of the fibrils may extend radially outwardly from the surface of the fibers in a central longitudinal third of at least some of the fibers. The fibers comprising the plurality of fibrils may be free of droplets of the lipid ester. The layer of fibers may comprise a plurality of bonds with each bond comprising a bond area. At least some of the plurality of fibrils may extend outwardly from a surface of at least one of the bond areas. The nonwoven substrate may comprise a second layer of fibers. The fibers of the second layer of fibers may be substantially free of, or free of, fibrils or may comprise a plurality of fibrils. In an example, the layer of fibers may comprise spunbond fibers and/or meltblown fibers and the second layer of fibers may comprise meltblown fibers and/or fine fibers. The fibrils may be a first color (e.g., blue, yellow) and the plurality of fibers may be a second color (e.g., light blue, green, red, teal) in non-fibril areas of the fibers. The first color and the second color may be the same or different.

TESTS

Surface Tension of a Liquid

The surface tension of a liquid is determined by measuring the force exerted on a platinum Wilhelmy plate at the air-liquid interface. A Kruss tensionmeter K11 or equivalent is used. (Available by Kruss USA (www.kruss.de)). The test is operated in a laboratory environment at 23±2° C. and 50±5% relative humidity. The test liquid is placed into the container given by the manufacturer and the surface tension is recorded by the instrument and its software.

Basis Weight Test

A 9.00 cm² large piece of nonwoven substrate, i.e., 1.0 cm wide by 9.0 cm long, is used. The sample may be cut out of a consumer product, such as a wipe or an absorbent article or a packaging material therefor. The sample needs to be dry and free from other materials like glue or dust. Samples are conditioned at 23° Celsius (±2° C.) and at a relative humidity of about 50% (±5%) for 2 hours to reach equilibrium. The weight of the cut nonwoven substrate is measured on a scale with accuracy to 0.0001 g. The resulting mass is divided by the specimen area to give a result in g/m² (gsm). Repeat the same procedure for at least 20 specimens from 20 identical consumer products or packaging materials therefor. If the consumer product or packaging materials therefor are large enough, more than one specimen can be obtained from each. An example of a sample is a portion of a topsheet of an absorbent article. If the local basis weight variation test is done, those same samples and data are used for calculating and reporting the average basis weight.

Fiber Diameter and Denier Test

The diameter of fibers in a sample of a nonwoven substrate is determined by using a Scanning Electron Microscope (SEM) and image analysis software. A magnification of 500 to 10,000 times is chosen such that the fibers are suitably enlarged for measurement. The samples are sputtered with gold or a palladium compound to avoid electric charging and vibrations of the fibers in the electron beam. A manual procedure for determining the fiber diameters is used. Using a mouse and a cursor tool, the edge of a randomly selected fiber is sought and then measured across its width (i.e., perpendicular to fiber direction at that point) to the other edge of the fiber. For non-circular fibers, the area of the cross-section is measured using the image analysis software. The effective diameter is then calculated by calculating the diameter as if the found area was that of a circle. A scaled and calibrated image analysis tool provides the scaling to get actual reading in micrometers (μm). Several fibers are thus randomly selected across the sample of the nonwoven substrate using the SEM. At least two specimens from the nonwoven substrate are cut and tested in this manner. Altogether, at least 100 such measurements are made and then all data is recorded for statistical analysis. The recorded data is used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

Fiber Diameter in denier=Cross-sectional area(in m²)*density(in kg/m³)*9000 m*1000 g/kg.

The cross-sectional area is $\pi$*diameter²/4. The density for polypropylene, for example, may be taken as 910 kg/m³.

Given the fiber diameter in denier, the physical circular fiber diameter in meters (or micrometers) is calculated from these relationships and vice versa. We denote the measured diameter (in microns) of an individual circular fiber as $d_f$.

In case the fibers have non-circular cross-sections, the measurement of the fiber diameter is determined as and set equal to the hydraulic diameter, as discussed above.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a nonwoven substrate that is placed on a reference absorbent pad. As a default, this is also called the 32 mN/m Low Surface Tension Fluid Strikethrough Test because of the surface tension of the test fluid and each test is done on two layers of the nonwoven substrate sample simply laid on top of each other.

For this test, the reference absorbent pad is 5 plies of Ahlstrom grade 989 filter paper (10 cm×10 cm) and the test fluid is a 32 mN/m low surface tension fluid.

Scope

This test is designed to characterize the low surface tension fluid strikethrough performance (in seconds) of nonwoven substrates intended to provide a barrier to low surface tension fluids, such as mixtures of urine and bowel movements or runny bowel movements for example.

Equipment

Figure 36:
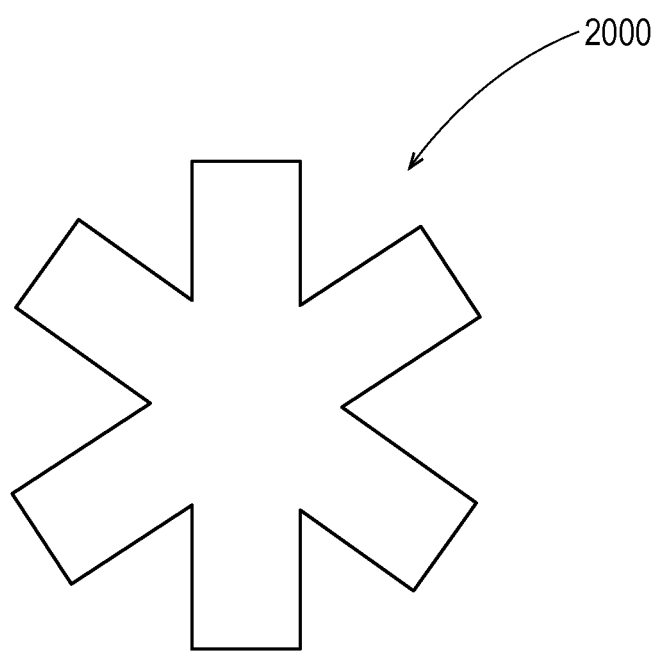
FIG. 36 is a view of an orifice used in the Low Surface Tension Fluid Strikethrough Time Test described herein.

Lister Strikethrough Tester: The instrumentation is the same as that described in EDANA ERT 153.0-02 section 6 with the following exception: the strike-through plate has a star-shaped orifice of 3 slots angled at 60 degrees with the narrow slots having a 10.0 mm length and a 1.2 mm slot width. The orifice 2000 is illustrated in FIG. 36. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

Ensure that the surface tension is 32 mN/m+/−1 mN/m according to the Surface Tension of a Liquid test described herein. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven substrate samples may be tested.

Cut the required number of nonwoven substrate specimens. For nonwoven substrates sampled off a roll, cut the samples into 10 cm by 10 cm sized square specimens. For nonwoven substrates sampled off of a consumer product, cut the samples into 15 by 15 mm square specimens. The fluid flows onto the nonwoven substrate specimen from the strike through plate. Touch the nonwoven substrate specimen only at the edge.

Neatly stack 5 plies of the Reference Absorbent Pad onto the base plate of the strikethrough tester.

Place the nonwoven substrate specimen on top of the 5 plies of filter paper. Two plies of the nonwoven substrate specimen are used in this test method. If the nonwoven substrate sample is sided (i.e., has a different layer configuration based on which side is facing in a particular direction), the side facing the wearer (for an absorbent product) faces upwards in the test.

Place the strikethrough plate over the nonwoven substrate specimen and ensure that the center of the strikethrough plate is over the center of the nonwoven substrate specimen. Center this assembly under the dispensing funnel.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for the required number of nonwoven substrate specimens. A minimum of 5 specimens of each different nonwoven substrate sample is required. The average value is the 32 mN/m low surface tension strikethrough time in seconds.

Specific Surface Area

The specific surface area of the nonwoven substrates of the present disclosure is determined by Krypton gas adsorption using a Micromeritic ASAP 2420 or equivalent instrument, using the continuous saturation vapor pressure (Po) method (according to ASTM D-6556-10), and following the principles and calculations of Brunauer, Emmett, and Teller, with a Kr-BET gas adsorption technique including automatic degas and thermal correction. Note that the specimens should not be degassed at 300 degrees Celsius as the method recommends, but instead should be degassed at room temperature. The specific surface area should be reported in $m^2/g$.

Obtaining Samples of Nonwoven Substrates

Each surface area measurement is taken from a specimen totaling 1 g of the nonwoven substrate of the present disclosure. In order to achieve 1 g of material, multiple specimens may be taken from one or more absorbent articles, one or more packages, or one or more wipes, depending on whether absorbent articles, packages, or wipes are being tested. Wet wipe specimens will be dried at 40 degrees C. for two hours or until liquid does not leak out of the specimen under light pressure. The specimens are cut from the absorbent articles, packages, or wipes (depending on whether absorbent articles, packages, or wipes are being tested) in areas free of, or substantially free of, adhesives using scissors. An ultraviolet fluorescence analysis cabinet is then used on the specimens to detect the presence of adhesives, as the adhesives will fluoresce under this light. Other methods of detecting the presence of adhesives may also be used. Areas of the specimens showing the presence of adhesives are cut away from the specimens, such that the specimens are free of the adhesives. The specimens may now be tested using the specific surface area method above.

Obtaining Samples of Nonwoven Barrier Cuffs

Each surface area measurement is made up of nonwoven barrier cuff (e.g., 50, 51) specimens taken from absorbent articles to reach a total sample mass of 1 g. The specimens are cut from the barrier cuffs in areas not directly bonded to the absorbent article (e.g., area 11 of FIG. 3) using scissors. An ultraviolet fluorescence analysis cabinet is then used on the specimens to detect for the presence of adhesive, as the adhesive will fluoresce under this light. Other methods of detecting the presence of adhesives may also be used. Areas of the specimens showing the presence of adhesive are cut away from the specimens, such that the specimens are free of the adhesives. The specimens may now be tested using the specific surface area method above.

Fibril Length Measurement Test

1) Using a software program such as Image J software, measure the number of pixels within the length of the legend on an SEM image of a nonwoven substrate using a straight line (i.e., a line with a length and no thickness). Record the length of the line and the number of microns that the legend corresponds to.

2) Pick a fibril and measure its length from its free end to the end originating out of the fiber as best visualized. Record the length of the line.

3) Divide this length by the length of the legend in pixels and then multiply by the length of the legend in microns to get the length of the fibril in microns.

If the fibrils are long and curly, then the length of such fibrils is taken in linear increments.

Mass-Average Diameter

The mass-average diameter of fibers is calculated as follows:

$$\text{mass average diameter, } d_{mass} = \frac{\sum_{i=1}^{n}(m_i \cdot d_i)}{\sum_{i=1}^{n} m_i}$$

$$= \frac{\sum_{i=1}^{n}(\rho \cdot V_i \cdot d_i)}{\sum_{i=1}^{n}(\rho \cdot V_i)}$$

$$= \frac{\sum_{i=1}^{n}\left(\rho \cdot \frac{\pi d_i^2 \cdot \partial x}{4} \cdot d_i\right)}{\sum_{i=1}^{n}\left(\rho \cdot \frac{\pi d_i^2 \cdot \partial x}{4}\right)}$$

$$= \frac{\sum_{i=1}^{n} d_i^3}{\sum_{i=1}^{n} d_i^2}$$

where
fibers in the sample are assumed to be circular/cylindrical,
$d_i$=measured diameter of the $i^{th}$ fiber in the sample,
$\partial x$=infinitesimal longitudinal section of fiber where its diameter is measured, same for all the fibers in the sample,
$m_i$=mass of the $i^{th}$ fiber in the sample,
n=number of fibers whose diameter is measured in the sample $\rho$=density of fibers in the sample, same for all the fibers in the sample
$V_i$=volume of the $i^{th}$ fiber in the sample.
The mass-average fiber diameter should be reported in μm.

Gravimetric Weight Loss Test

The Gravimetric Weight Loss Test is used to determine the amount of lipid ester (e.g., GTS) in a nonwoven substrate of the present disclosure. One or more samples of the nonwoven substrate are placed, with the narrowest sample dimension no greater than 1 mm, into acetone at a ratio of 1 g nonwoven substrate sample per 100 g of acetone using a refluxing flask system. First, the sample is weighed before being placed into the reflux flask, and then the mixture of the sample and the acetone is heated to 60° C. for 20 hours. The sample is then removed and air dried for 60 minutes and a final weight of the sample is determined. The equation for calculating the weight percent lipid ester in the sample is:

weight%lipid ester=([initial mass of the sample−final mass of the sample]/[initial mass of the sample])×100%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patents or patent applications, are hereby incorporated by reference in their entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, those of skill in the art will recognize that various other changes and modifications can be made without departing from the spirit and scope of the invention. It is therefore intended to cover in the appended claims all such changes and modifications that are within the scope of this invention.

What is claimed is:

1. An absorbent article comprising:
    a liquid pervious material;
    a liquid impervious material;
    an absorbent core disposed at least partially intermediate the liquid pervious material and the liquid impervious material; and
    a nonwoven substrate comprising a layer of fibers, wherein a plurality of the fibers each comprise a plurality of fibrils extending outwardly from a surface of the fibers, wherein the plurality of fibrils comprise a lipid ester, and wherein the plurality of the fibrils grow out of the surface of the fibers at least 24 hours post-nonwoven substrate formation under ambient conditions.

2. The absorbent article of claim 1, wherein the liquid impervious material comprises the nonwoven substrate, and wherein the liquid impervious material is free of a film.

3. The absorbent article of claim 1, wherein a portion of the liquid pervious material comprises the nonwoven substrate.

4. The absorbent article of claim 1, comprising a barrier leg cuff, wherein a portion of the barrier leg cuff comprises the nonwoven substrate, and wherein the barrier leg cuff is free of a film.

5. The absorbent article of claim 1, wherein the plurality of fibrils consist essentially of the lipid ester.

6. The absorbent article of claim 1, wherein the plurality of fibers are formed from a composition comprising a polyolefin and the lipid ester, and wherein the composition comprises at least 11% of the lipid ester, by weight of the composition.

7. The absorbent article of claim 6, wherein the lipid ester has a melting point in the range of 40° C. to 150° C.

8. The absorbent article of claim 1, wherein an average length of the fibrils from the surfaces of the fibers to free ends of the fibrils is in the range of about 0.5 µm to about 20 µm.

9. The absorbent article of claim 1, wherein an average hydraulic diameter of the fibrils is in the range of about 100 nm to about 800 nm.

10. The absorbent article of claim 1, wherein the layer of fibers comprises spunbond fibers, meltblown fibers, or fine fibers.

11. The absorbent article of claim 1, wherein at least some of the fibrils extend radially outwardly from the surface of the fibers in a central longitudinal third of at least some of the fibers.

12. The absorbent article of claim 1, wherein the fibers comprising the plurality of fibrils are free of droplets of the lipid ester.

13. An absorbent article comprising:
a liquid pervious material;
a liquid impervious material;
an absorbent material positioned at least partially intermediate the liquid pervious material and the liquid impervious material; and
a nonwoven substrate comprising a layer of fibers, wherein the layer of fibers comprises a plurality of bonds, each bond comprising a bond area, wherein a plurality of fibrils extend outwardly from a surface of at least one of the bond areas, and wherein the plurality of the fibrils grow out of the surface of the at least one of the bond areas at least 24 hours post-nonwoven substrate formation under ambient conditions.

14. The absorbent article of claim 13, wherein the plurality of fibrils consist essentially of a lipid ester.

15. The absorbent article of claim 13, wherein the plurality of fibrils comprise glycerol tristearate, and wherein the glycerol tristearate has a melting temperature above 35° C.

16. The absorbent article of claim 13, wherein a plurality of the fibers comprise fibrils extending radially outwardly from a surface of the fibers.

17. The absorbent article of claim 16, wherein the nonwoven substrate comprises a second layer of fibers, and wherein the fibers of the second layer of fibers are substantially free of fibrils.

18. The absorbent article of claim 16, wherein the nonwoven substrate comprises a second layer of fibers, and wherein a plurality of fibrils extend radially outwardly from a surface of at least some of the fibers in the second layer of fibers.

19. The absorbent article of claim 16, wherein the nonwoven substrate comprises a second layer of fibers, wherein the layer of fibers comprises spunbond fibers, and wherein the second layer of fibers comprises meltblown fibers or fine fibers.

20. The absorbent article of claim 13, wherein the fibers are formed from a composition comprising at least 11% of a lipid ester, by weight of the composition.

21. An absorbent article comprising:
a nonwoven substrate comprising a layer of fibers, wherein a plurality of the fibers comprise fibrils extending outwardly therefrom only after a time period, and wherein the time period is greater than about 24 hours post-nonwoven substrate formation under ambient conditions.

22. The absorbent article of claim 21, wherein the time period is greater than about 100 hours post-nonwoven substrate formation under ambient conditions.

23. The absorbent article of claim 21, wherein the fibrils are a first color, wherein the plurality of fibers in non-fibril areas are a second color, and wherein the first color and the second color are different.

24. The absorbent article of claim 21, wherein the plurality of fibers are free of droplets of a lipid ester.

25. The absorbent article of claim 21, comprising:
a liquid pervious material;
a liquid impervious material; and
an absorbent core disposed at least partially intermediate the liquid pervious material and the liquid impervious material;
wherein the fibrils comprise a lipid ester.

26. The absorbent article of claim 25, wherein the liquid impervious material comprises the nonwoven substrate, and wherein the liquid impervious material is free of a film.

27. The absorbent article of claim 25, wherein a portion of the liquid pervious material comprises the nonwoven substrate.

28. The absorbent article of claim 25, comprising a barrier leg cuff, wherein a portion of the barrier leg cuff comprises the nonwoven substrate, and wherein the barrier leg cuff is free of a film.

29. The absorbent article of claim 21, wherein the fibrils consist essentially of a lipid ester.

30. The absorbent article of claim 21, wherein the plurality of fibers are formed from a composition comprising a polyolefin and a lipid ester, and wherein the composition comprises at least 11% of the lipid ester, by weight of the composition.

31. The absorbent article of claim 30, wherein the lipid ester has a melting point in the range of 40° C. to 150° C.

32. The absorbent article of claim 21, wherein an average length of the fibrils from a surface of the fibers to free ends of the fibrils is in the range of about 0.5 µm to about 20 µm.

33. The absorbent article of claim 21, wherein an average hydraulic diameter of the fibrils is in the range of about 100 nm to about 800 nm.

34. The absorbent article of claim 21, wherein at least some of the fibrils extend radially outwardly from a surface of the plurality of fibers in a central longitudinal third of at least some of the plurality of fibers.

35. The absorbent article of claim 21, wherein the fibers comprising the fibrils are free of droplets of a lipid ester.

36. An absorbent article comprising:
a liquid pervious material;
a liquid impervious material;
an absorbent core disposed at least partially intermediate the liquid pervious material and the liquid impervious material; and
a nonwoven substrate comprising a layer of fibers, wherein a plurality of the fibers each comprise a plurality of fibrils extending outwardly from a surface of the fibers, and wherein the plurality of fibrils grow out of the surface of the fibers at least 24 hours post-nonwoven substrate formation under ambient conditions.

37. The absorbent article of claim 36, wherein the plurality of fibrils comprise a lipid ester.

38. The absorbent article of claim 36, wherein the plurality of fibrils consist essentially of a lipid ester.

39. The absorbent article of claim 36, wherein the plurality of fibrils are a first color, wherein the plurality of fibers are a second color in non-fibril areas, and wherein the first color and the second color are different.

* * * * *